(12) United States Patent
Graddis et al.

(10) Patent No.: US 7,067,118 B2
(45) Date of Patent: Jun. 27, 2006

(54) METHODS OF USING MUTANT FLT3-LIGAND POLYPEPTIDES TO INDUCE CELLULAR EXPANSION

(75) Inventors: Thomas J. Graddis, Cupertino, CA (US); Jeffrey T. McGrew, Seattle, WA (US)

(73) Assignee: Immunex Corporation, Seattle, WA (US)

( * ) Notice: Subject to any disclaimer, the term of this patent is extended or adjusted under 35 U.S.C. 154(b) by 0 days.

(21) Appl. No.: 09/904,536

(22) Filed: Jul. 16, 2001

(65) Prior Publication Data

US 2002/0111475 A1 Aug. 15, 2002

Related U.S. Application Data

(62) Division of application No. 09/109,100, filed on Jul. 2, 1998, now Pat. No. 6,291,661.

(51) Int. Cl.
*A61K 38/19* (2006.01)
(52) U.S. Cl. .............. 424/85.1; 424/198.1; 514/2; 530/351
(58) Field of Classification Search ............ 514/2; 424/85.1, 198.1; 530/351, 399
See application file for complete search history.

(56) References Cited

U.S. PATENT DOCUMENTS

| 5,073,627 A | 12/1991 | Curtis et al. |
| 5,554,512 A | 9/1996 | Lyman et al. |
| 5,843,423 A * | 12/1998 | Lyman et al. ............ 424/85.1 |

FOREIGN PATENT DOCUMENTS

| EP | 0 627 487 | 12/1994 |
| WO | WO 97/12633 | 4/1997 |
| WO | WO 97/38101 | 10/1997 |
| WO | WO 98/18923 | 5/1998 |

OTHER PUBLICATIONS

E. Maraskovsky et al., "Dramatic increase in the numbers of functionally mature dendritic cells in Flt3 ligand-treated mice: Multiple dendritic cell subpopulations identified", J. Exp. Med. 184:1953-1962, Nov. 1996.*

Stewart Lyman et al., "Cloning of the Human Homologue of the Murine flt3 Ligand: A Growth Factor for Early Hematopoietic Progenitor Cells," *Blood*, vol. 83, No. 10, May 15, 1994, pp. 2795-2801.

K. Brasel et al., "Expression of the flt3 receptor and its ligand on hematopoietic cells," *Leukemia*, 1995, vol. 9, pp. 1212-1218.

Jayvardhan Pandit et al., "Three-Dimensional Structure of Dimeric Human Recombinant Macrophage Colony-Stimulating Factor," *Science*, vol. 258, Nov. 20, 1992, pp. 1358-1362.

C. Hannum et al., "Ligand for FLT3/FLK2 receptor tyrosine kinase regulates growth of haematopoietic stem cells and is encoded by variant RNAs," *Nature*, vol. 368, Apr. 14, 1994, pp. 643-648.

Stewart D. Lyman et al., "Molecular Cloning of a Ligand for the flt3/flk-2 Tyrosine Kinase Receptor: A Proliferative Factor for Primitive Hematopoietic Cells," *Cell*, vol. 75, Dec. 17, 1993, pp. 1157-1167.

Donald Small et al., "STK-1, the human homolog of Flk-2/Flt-3, is selectively expressed in CD34[+] human bone marrow cells and is involved in the proliferation of early progenitor/stem cells," *Proc. Nat'l. Acad. Sci.*, U.S.A., vol. 91, Jan. 1994, pp. 459-463, Cell Biology.

Stewart D. Lyman et al., "Biology of flt3 and receptor," *Int'l. J. of Hematology*, vol. 62 (1995), pp. 63-73.

Jeffrey T. McGrew et al., "Expression of trimeric CD40 ligand in *Pichia pastoris*: use of a rapid method to detect high-level expressing transformats," *Gene*, vol. 187, (1997), pp. 193-200.

(Continued)

*Primary Examiner*—Lorraine Spector
(74) *Attorney, Agent, or Firm*—Finnegan, Henderson, Farabow, Garrett & Dunner, LLP

(57) ABSTRACT

A screening method for identifying mutant polypeptides having at least one amino acid difference from a wild type protein involved in a receptor-ligand interaction is disclosed. Also disclosed are mutant polypeptides of the hematopoietic growth factor flt3-Ligand (flt3-L) identified using this method, nucleic acids encoding these flt3-L mutant polypeptides, and methods of treatment involving in vitro and in vivo use of the mutant polypeptides and nucleic acids.

54 Claims, 6 Drawing Sheets

OTHER PUBLICATIONS

Arne Skerra et al., "Filter Screening of Antibody Fab Fragments Secreted from Individual Bacterial Colonies: Specific Detection of Antigen Binding with a Two-Membrane System," *Analytical Biochemistry*, vol. 196 (1991), pp. 151-155.

James A. Wells, "Additivity of Mutational Effects in Proteins," *Biochemistry*, vol. 29, No. 37, Sep. 18, 1990, pp. 8509-8517.

Sten E. W. Jacobson, et al., "The FLT3 Ligand Potently and Directly Stimulates the Growth and Expansion of Primitive Murine Bone Marrow Progenitor Cells in Vitro: Synergistic Interactions with Interleukin (IL) 11, IL-12, and Other Hematopoietic Growth Factors," *J. Exp. Med.*, vol. 181, pp. 1357-1363 (Apr. 1995).

Stewart D. Lyman et al., "Identification of soluble and membrane-bound isoforms of the murine flt3 ligand generated by alternative splicing of mRNAs," *Oncogene*, vol. 10 (1995), pp. 149-157.

T. Graddis et al., "Structure-function analysis of FLT3 ligand FLT3 receptor interactions using a rapid functional screen," *J. Biol. Chem.*, vol. 273, No. 28, pp. 17626-17633 (1998).

* cited by examiner

```
hflt3L  .TQDCSFQHSPISSDFAVKIRELSDYLLQDYPVTVASNLQDEE..
mflt3L  .-P--Y-S----N-K--F--T-H--K-----V----K...
hM-CSF  EEVSEYCSHMIGSHLQSLQRLIDSQMETSCQITFEFVDQEQLKDP
                                  bbbbb
                    Helix A hflt3L  LCGGLWRLVLAQRWMERLKTVAGS.KMQGLLERVNTEIHFVTKCAFQPPPS..
mflt3L  H--KA--S-F----I-Q-------------T--D-----------S-T--L-E..
hM-CSF  VCYLKKAFLLVQDIMEDTMRFRDNTPNAIAIVQLELSLPLKSCFTKDYEEHD
         aaaaaaaaaaaaaaaaa              aaaaaaaaaaa
              Helix B                    Helix C hflt3L  ..CLRFVQTNISRLLQETSEQLVALKPWITR...QNFsRCLE..LQCQP
mflt3L  ..-----------H--KD-CT--L----C-GK.AC------.-V---
hM-CSF  KACVRTFYETPLQLLEKVKNVFNETKNLLDKDWNIFSKNCNNSFAECSSQ
         bbbbb         aaaaaaaaaaaaaaa
                        Helix D
```

FIG.1

SEQUENCE LISTING

<160> NUMBER OF SEQ ID NOS: 20

<210> SEQ ID NO 1
<211> LENGTH: 235
<212> TYPE: PRT
<213> ORGANISM: Homo sapiens

<400> SEQUENCE: 1

Met Thr Val Leu Ala Pro Ala Trp Ser Pro Thr Thr Tyr Leu Leu Leu
1               5                   10                  15

Leu Leu Leu Leu Ser Ser Gly Leu Ser Gly Thr Gln Asp Cys Ser Phe
            20                  25                  30

Gln His Ser Pro Ile Ser Ser Asp Phe Ala Val Lys Ile Arg Glu Leu
        35                  40                  45

Ser Asp Tyr Leu Leu Gln Asp Tyr Pro Val Thr Val Ala Ser Asn Leu
    50                  55                  60

Gln Asp Glu Glu Leu Cys Gly Gly Leu Trp Arg Leu Val Leu Ala Gln
65                  70                  75                  80

Arg Trp Met Glu Arg Leu Lys Thr Val Ala Gly Ser Lys Met Gln Gly
                85                  90                  95

Leu Leu Glu Arg Val Asn Thr Glu Ile His Phe Val Thr Lys Cys Ala
            100                 105                 110

Phe Gln Pro Pro Pro Ser Cys Leu Arg Phe Val Gln Thr Asn Ile Ser
        115                 120                 125

Arg Leu Leu Gln Glu Thr Ser Glu Gln Leu Val Ala Leu Lys Pro Trp
    130                 135                 140

Ile Thr Arg Gln Asn Phe Ser Arg Cys Leu Glu Leu Gln Cys Gln Pro
145                 150                 155                 160

Asp Ser Ser Thr Leu Pro Pro Pro Trp Ser Pro Arg Pro Leu Glu Ala
                165                 170                 175

Thr Ala Pro Thr Ala Pro Gln Pro Pro Leu Leu Leu Leu Leu Leu Leu
            180                 185                 190

Pro Val Gly Leu Leu Leu Ala Ala Ala Trp Cys Leu His Trp Gln
        195                 200                 205

Arg Thr Arg Arg Arg Thr Pro Arg Pro Gly Glu Gln Val Pro Pro Val
    210                 215                 220

Pro Ser Pro Gln Asp Leu Leu Leu Val Glu His
225                 230                 235

<210> SEQ ID NO 2
<211> LENGTH: 988
<212> TYPE: DNA
<213> ORGANISM: Homo sapiens
<220> FEATURE:
<221> NAME/KEY: CDS
<222> LOCATION: (30)..(734)

<400> SEQUENCE: 2
cggccggaat tccggggccc ccggccgaa atg aca gtg ctg gcg cca gcc tgg     53
                                Met Thr Val Leu Ala Pro Ala Trp
                                 1               5 agc cca aca acc tat ctc ctc ctg ctg ctg ctg agc tcg gga ctc        101
Ser Pro Thr Thr Tyr Leu Leu Leu Leu Leu Leu Ser Ser Gly Leu
        10                  15                  20 agt ggg acc cag gac tgc tcc ttc caa cac agc ccc atc tcc tcc gac    149
Ser Gly Thr Gln Asp Cys Ser Phe Gln His Ser Pro Ile Ser Ser Asp
 25                  30                  35                  40

|   |   |   |   |   |   |   |   |   |   |   |   |   |   |   |   |     |
|---|---|---|---|---|---|---|---|---|---|---|---|---|---|---|---|-----|
| ttc | gct | gtc | aaa | atc | cgt | gag | ctg | tct | gac | tac | ctg | ctt | caa | gat | tac | 197 |
| Phe | Ala | Val | Lys | Ile | Arg | Glu | Leu | Ser | Asp | Tyr | Leu | Leu | Gln | Asp | Tyr |     |
|     |     |     |     | 45  |     |     |     | 50  |     |     |     |     | 55  |     |     |     |
| cca | gtc | acc | gtg | gcc | tcc | aac | ctg | cag | gac | gag | gag | ctc | tgc | ggg | ggc | 245 |
| Pro | Val | Thr | Val | Ala | Ser | Asn | Leu | Gln | Asp | Glu | Glu | Leu | Cys | Gly | Gly |     |
|     |     |     | 60  |     |     |     |     | 65  |     |     |     |     | 70  |     |     |     |
| ctc | tgg | cgg | ctg | gtc | ctg | gca | cag | cgc | tgg | atg | gag | cgg | ctc | aag | act | 293 |
| Leu | Trp | Arg | Leu | Val | Leu | Ala | Gln | Arg | Trp | Met | Glu | Arg | Leu | Lys | Thr |     |
|     |     | 75  |     |     |     |     | 80  |     |     |     |     | 85  |     |     |     |     |
| gtc | gct | ggg | tcc | aag | atg | caa | ggc | ttg | ctg | gag | cgc | gtg | aac | acg | gag | 341 |
| Val | Ala | Gly | Ser | Lys | Met | Gln | Gly | Leu | Leu | Glu | Arg | Val | Asn | Thr | Glu |     |
| 90  |     |     |     |     | 95  |     |     |     |     | 100 |     |     |     |     |     |     |
| ata | cac | ttt | gtc | acc | aaa | tgt | gcc | ttt | cag | ccc | ccc | ccc | agc | tgt | ctt | 389 |
| Ile | His | Phe | Val | Thr | Lys | Cys | Ala | Phe | Gln | Pro | Pro | Pro | Ser | Cys | Leu |     |
| 105 |     |     |     | 110 |     |     |     |     | 115 |     |     |     |     | 120 |     |     |
| cgc | ttc | gtc | cag | acc | aac | atc | tcc | cgc | ctc | ctg | cag | gag | acc | tcc | gag | 437 |
| Arg | Phe | Val | Gln | Thr | Asn | Ile | Ser | Arg | Leu | Leu | Gln | Glu | Thr | Ser | Glu |     |
|     |     |     |     | 125 |     |     |     |     | 130 |     |     |     |     | 135 |     |     |
| cag | ctg | gtg | gcg | ctg | aag | ccc | tgg | atc | act | cgc | cag | aac | ttc | tcc | cgg | 485 |
| Gln | Leu | Val | Ala | Leu | Lys | Pro | Trp | Ile | Thr | Arg | Gln | Asn | Phe | Ser | Arg |     |
|     |     | 140 |     |     |     |     | 145 |     |     |     |     | 150 |     |     |     |     |
| tgc | ctg | gag | ctg | cag | tgt | cag | ccc | gac | tcc | tca | acc | ctg | cca | ccc | cca | 533 |
| Cys | Leu | Glu | Leu | Gln | Cys | Gln | Pro | Asp | Ser | Ser | Thr | Leu | Pro | Pro | Pro |     |
|     | 155 |     |     |     |     | 160 |     |     |     |     | 165 |     |     |     |     |     |
| tgg | agt | ccc | cgg | ccc | ctg | gag | gcc | aca | gcc | ccg | aca | gcc | ccg | cag | ccc | 581 |
| Trp | Ser | Pro | Arg | Pro | Leu | Glu | Ala | Thr | Ala | Pro | Thr | Ala | Pro | Gln | Pro |     |
| 170 |     |     |     |     | 175 |     |     |     |     | 180 |     |     |     |     |     |     |
| cct | ctc | ctc | ctc | cta | ctg | ctg | ccc | gtg | ggc | ctc | ctg | ctg | ctg | gcc |     | 629 |
| Pro | Leu | Leu | Leu | Leu | Leu | Leu | Pro | Val | Gly | Leu | Leu | Leu | Leu | Ala |     |     |
| 185 |     |     |     |     | 190 |     |     |     |     | 195 |     |     |     | 200 |     |     |
| gct | gcc | tgg | tgc | ctg | cac | tgg | cag | agg | acg | cgg | cgg | agg | aca | ccc | cgc | 677 |
| Ala | Ala | Trp | Cys | Leu | His | Trp | Gln | Arg | Thr | Arg | Arg | Arg | Thr | Pro | Arg |     |
|     |     |     |     | 205 |     |     |     |     | 210 |     |     |     |     | 215 |     |     |
| cct | ggg | gag | cag | gtg | ccc | ccc | gtc | ccc | agt | ccc | cag | gac | ctg | ctg | ctt | 725 |
| Pro | Gly | Glu | Gln | Val | Pro | Pro | Val | Pro | Ser | Pro | Gln | Asp | Leu | Leu | Leu |     |
|     |     | 220 |     |     |     |     | 225 |     |     |     |     | 230 |     |     |     |     |
| gtg | gag | cac | tgacctggcc aaggcctcat cctgcggagc cttaaacaac | | | | | | | | | | | | 774 |
| Val | Glu | His |   |   |   |   |   |   |   |   |   |   |   |   |   |     |
|     |     | 235 |   |   |   |   |   |   |   |   |   |   |   |   |   |     |

| | |
|---|---|
| gcagtgagac agacatctat catcccattt tacaggggag gatactgagg cacacagagg | 834 |
| ggagtcacca gccagaggat gtatagcctg gacacagagg aagttggcta gaggccggtc | 894 |
| ccttccttgg gccctctca ttccctcccc agaatggagg caacgccaga atccagcacc | 954 |
| ggccccattt acccaactct gaacaaagcc cccg | 988 |

<210> SEQ ID NO 3
<211> LENGTH: 40
<212> TYPE: DNA
<213> ORGANISM: Artificial Sequence
<220> FEATURE:
<223> OTHER INFORMATION: Description of Artificial Sequence: primer

<400> SEQUENCE: 3
attaggtacc tttggataaa agactcagtg ggaccaggac          40

<210> SEQ ID NO 4
<211> LENGTH: 37
<212> TYPE: DNA
<213> ORGANISM: Artificial Sequence
<220> FEATURE:

<223> OTHER INFORMATION: Description of Artificial Sequence: primer

<400> SEQUENCE: 4
atatggatcc ctacggggct gtggcctcca ggggccg                           37

<210> SEQ ID NO 5
<211> LENGTH: 77
<212> TYPE: DNA
<213> ORGANISM: Artificial Sequence
<220> FEATURE:
<223> OTHER INFORMATION: Description of Artificial Sequence: primer

<400> SEQUENCE: 5
cctcctgcag gagacctccg agcagctggt ggcgctgaag ccctggatca ctcgccagaa    60
cttcgcccgg tgcctgg                                                  77

<210> SEQ ID NO 6
<211> LENGTH: 46
<212> TYPE: DNA
<213> ORGANISM: Artificial Sequence
<220> FEATURE:
<223> OTHER INFORMATION: Description of Artificial Sequence:
      constructed oligonucleotide

<400> SEQUENCE: 6
tggataaaag acacagtggg acccaggact gctccttcca atacag                  46

<210> SEQ ID NO 7
<211> LENGTH: 46
<212> TYPE: DNA
<213> ORGANISM: Artificial Sequence
<220> FEATURE:
<223> OTHER INFORMATION: Description of Artificial Sequence:
      constructed oligonucleotide

<400> SEQUENCE: 7
tggataaaag acacagtggg acccaggact gctccttcca atacag                  46

<210> SEQ ID NO 8
<211> LENGTH: 209
<212> TYPE: PRT
<213> ORGANISM: Homo sapiens

<400> SEQUENCE: 8

Thr Gln Asp Cys Ser Phe Gln Arg Ser Pro Ile Ser Ser Asp Phe Ala
 1               5                  10                  15

Val Lys Ile Arg Glu Leu Ser Asp Tyr Leu Leu Gln Asp Tyr Pro Val
                20                  25                  30

Thr Val Ala Ser Asn Leu Gln Asp Glu Glu Leu Cys Gly Gly Leu Trp
            35                  40                  45

Arg Leu Val Leu Ala Gln Arg Trp Met Glu Arg Leu Lys Thr Val Ala
        50                  55                  60

Gly Ser Lys Met Gln Gly Leu Leu Glu Arg Val Asn Thr Glu Ile His
 65                  70                  75                  80

Phe Val Thr Lys Cys Ala Phe Gln Pro Pro Pro Ser Cys Leu Arg Phe
                85                  90                  95

Val Gln Thr Asn Ile Ser Arg Leu Leu Gln Glu Thr Ser Glu Gln Leu
               100                 105                 110

Val Ala Leu Lys Pro Trp Ile Thr Arg Gln Asn Phe Ser Arg Cys Leu
           115                 120                 125

Glu Leu Gln Cys Gln Pro Asp Ser Ser Thr Leu Pro Pro Pro Trp Ser

```
            130                 135                 140
Pro Arg Pro Leu Glu Ala Thr Ala Pro Thr Ala Pro Gln Pro Leu
145                 150                 155                 160

Leu Leu Leu Leu Leu Leu Pro Val Gly Leu Leu Leu Ala Ala Ala
                165                 170                 175

Trp Cys Leu His Trp Gln Arg Thr Arg Arg Thr Pro Arg Pro Gly
            180                 185                 190

Glu Gln Val Pro Pro Val Pro Ser Pro Gln Asp Leu Leu Leu Val Glu
                195                 200                 205

His

<210> SEQ ID NO 9
<211> LENGTH: 209
<212> TYPE: PRT
<213> ORGANISM: Homo sapiens

<400> SEQUENCE: 9

Thr Gln Asp Cys Ser Phe Gln His Ser Pro Ile Ser Ser Asp Phe Ala
1               5                   10                  15

Val Lys Ile Arg Glu Leu Ser Asp Tyr Leu Leu Gln Asp Tyr Pro Val
                20                  25                  30

Thr Val Ala Ser Asn Leu Gln Asp Glu Glu Leu Cys Gly Gly Leu Trp
            35                  40                  45

Arg Leu Val Leu Ala Gln Arg Trp Met Glu Arg Leu Lys Thr Val Thr
        50                  55                  60

Gly Ser Lys Met Gln Gly Leu Leu Glu Arg Val Asn Thr Glu Ile His
65                  70                  75                  80

Phe Val Thr Lys Cys Ala Phe Gln Pro Pro Pro Ser Cys Leu Arg Phe
                85                  90                  95

Val Gln Thr Asn Ile Ser Arg Leu Leu Gln Glu Thr Ser Glu Gln Leu
                100                 105                 110

Val Ala Leu Lys Pro Trp Ile Thr Arg Gln Asn Phe Ser Arg Cys Leu
            115                 120                 125

Glu Leu Gln Cys Gln Pro Asp Ser Ser Thr Leu Pro Pro Pro Trp Ser
        130                 135                 140

Pro Arg Pro Leu Glu Ala Thr Ala Pro Thr Ala Pro Gln Pro Leu
145                 150                 155                 160

Leu Leu Leu Leu Leu Leu Pro Val Gly Leu Leu Leu Ala Ala Ala
                165                 170                 175

Trp Cys Leu His Trp Gln Arg Thr Arg Arg Thr Pro Arg Pro Gly
            180                 185                 190

Glu Gln Val Pro Pro Val Pro Ser Pro Gln Asp Leu Leu Leu Val Glu
                195                 200                 205

His

<210> SEQ ID NO 10
<211> LENGTH: 212
<212> TYPE: PRT
<213> ORGANISM: Homo sapiens

<400> SEQUENCE: 10

His Ser Gly Thr Gln Asp Cys Ser Phe Gln His Ser Pro Ile Ser Ser
1               5                   10                  15

Asp Phe Ala Val Lys Ile Arg Glu Leu Ser Asp Tyr Leu Leu Gln Asp
                20                  25                  30
```

```
Tyr Pro Val Thr Val Ala Ser Asn Leu Gln Asp Glu Glu Leu Cys Gly
         35                  40                  45

Gly Leu Trp Arg Leu Val Leu Ala Gln Arg Trp Met Glu Arg Leu Lys
 50                  55                  60

Thr Val Ala Gly Ser Lys Met Gln Gly Leu Leu Glu Arg Val Asn Thr
 65                  70                  75                  80

Glu Ile His Phe Val Thr Lys Cys Ala Phe Gln Pro Pro Ser Cys
                 85                  90                  95

Leu Arg Phe Val Gln Thr Asn Ile Ser Arg Leu Leu Gln Glu Thr Ser
                100                 105                 110

Glu Gln Leu Val Ala Leu Lys Pro Trp Ile Thr Arg Gln Asn Phe Ser
            115                 120                 125

Arg Cys Leu Glu Leu Gln Cys Gln Pro Asp Ser Ser Thr Leu Pro Pro
130                 135                 140

Pro Trp Ser Pro Arg Pro Leu Glu Ala Thr Ala Pro Thr Ala Pro Gln
145                 150                 155                 160

Pro Pro Leu Leu Leu Leu Leu Leu Pro Val Gly Leu Leu Leu Leu
                165                 170                 175

Ala Ala Ala Trp Cys Leu His Trp Gln Arg Thr Arg Arg Thr Pro
            180                 185                 190

Arg Pro Gly Glu Gln Val Pro Pro Val Pro Ser Pro Gln Asp Leu Leu
            195                 200                 205

Leu Val Glu His
    210

<210> SEQ ID NO 11
<211> LENGTH: 209
<212> TYPE: PRT
<213> ORGANISM: Homo sapiens

<400> SEQUENCE: 11

Thr Gln Asp Cys Ser Phe Gln Tyr Ser Pro Ile Ser Ser Asp Phe Ala
 1               5                  10                  15

Val Lys Ile Arg Glu Leu Ser Asp Tyr Leu Leu Gln Asp Tyr Pro Val
            20                  25                  30

Thr Val Ala Ser Asn Leu Gln Asp Glu Glu Leu Cys Gly Gly Leu Trp
         35                  40                  45

Arg Leu Val Leu Ala Gln Arg Trp Met Glu Arg Leu Lys Thr Val Ala
 50                  55                  60

Gly Ser Lys Met Gln Gly Leu Leu Glu Arg Val Asn Thr Glu Ile His
 65                  70                  75                  80

Phe Val Thr Lys Cys Ala Phe Gln Pro Pro Ser Cys Leu Arg Phe
                 85                  90                  95

Val Gln Thr Asn Ile Ser Arg Leu Leu Gln Glu Thr Ser Glu Gln Leu
                100                 105                 110

Val Ala Leu Lys Pro Trp Ile Thr Arg Gln Asn Phe Ser Arg Cys Leu
            115                 120                 125

Glu Leu Gln Cys Gln Pro Asp Ser Ser Thr Leu Pro Pro Pro Trp Ser
130                 135                 140

Pro Arg Pro Leu Glu Ala Thr Ala Pro Thr Ala Pro Gln Pro Pro Leu
145                 150                 155                 160

Leu Leu Leu Leu Leu Pro Val Gly Leu Leu Leu Ala Ala Ala
                165                 170                 175

Trp Cys Leu His Trp Gln Arg Thr Arg Arg Thr Pro Arg Pro Gly
            180                 185                 190
```

```
Glu Gln Val Pro Pro Val Pro Ser Pro Gln Asp Leu Leu Leu Val Glu
        195                 200                 205

His

<210> SEQ ID NO 12
<211> LENGTH: 209
<212> TYPE: PRT
<213> ORGANISM: Homo sapiens

<400> SEQUENCE: 12

Thr Gln Asp Cys Ser Phe Gln His Ser Pro Ile Ser Ser Asp Phe Ala
 1               5                  10                  15

Val Lys Ile Arg Glu Leu Ser Asp Tyr Phe Leu Gln Asp Tyr Pro Val
                20                  25                  30

Thr Val Ala Ser Asn Leu Gln Asp Glu Glu Leu Cys Gly Gly Leu Trp
            35                  40                  45

Arg Leu Val Leu Ala Gln Arg Trp Met Glu Arg Leu Lys Thr Val Ala
    50                  55                  60

Gly Ser Lys Met Gln Gly Leu Leu Glu Arg Val Asn Thr Glu Ile His
65                  70                  75                  80

Phe Val Thr Lys Cys Ala Phe Gln Pro Pro Ser Cys Leu Arg Phe
                85                  90                  95

Val Gln Thr Asn Ile Ser Arg Leu Leu Gln Glu Thr Ser Glu Gln Leu
                100                 105                 110

Val Ala Leu Lys Pro Trp Ile Thr Arg Gln Asn Phe Ser Arg Cys Leu
            115                 120                 125

Glu Leu Gln Cys Gln Pro Asp Ser Ser Thr Leu Pro Pro Pro Trp Ser
    130                 135                 140

Pro Arg Pro Leu Glu Ala Thr Ala Pro Thr Ala Pro Gln Pro Pro Leu
145                 150                 155                 160

Leu Leu Leu Leu Leu Leu Pro Val Gly Leu Leu Leu Ala Ala Ala
                165                 170                 175

Trp Cys Leu His Trp Gln Arg Thr Arg Arg Arg Thr Pro Arg Pro Gly
            180                 185                 190

Glu Gln Val Pro Pro Val Pro Ser Pro Gln Asp Leu Leu Leu Val Glu
        195                 200                 205

His

<210> SEQ ID NO 13
<211> LENGTH: 209
<212> TYPE: PRT
<213> ORGANISM: Homo sapiens

<400> SEQUENCE: 13

Thr Gln Asp Cys Ser Phe Gln His Ser Pro Ile Ser Ser Asp Phe Ala
 1               5                  10                  15

Val Lys Ile Arg Glu Leu Ser Asp Tyr Leu Pro Gln Asp Tyr Pro Val
                20                  25                  30

Thr Val Ala Ser Asn Leu Gln Asp Glu Glu Leu Cys Gly Gly Leu Trp
            35                  40                  45

Arg Leu Val Leu Ala Gln Arg Trp Met Glu Arg Leu Lys Thr Val Ala
    50                  55                  60

Gly Ser Lys Met Gln Gly Leu Leu Glu Arg Val Asn Thr Glu Ile His
65                  70                  75                  80

Phe Val Thr Lys Cys Ala Phe Gln Pro Pro Ser Cys Leu Arg Phe
```

-continued

```
                85                  90                  95
Val Gln Thr Asn Ile Ser Arg Leu Leu Gln Glu Thr Ser Glu Gln Leu
            100                 105                 110
Val Ala Leu Lys Pro Trp Ile Thr Arg Gln Asn Phe Ser Arg Cys Leu
            115                 120                 125
Glu Leu Gln Cys Gln Pro Asp Ser Ser Thr Leu Pro Pro Pro Trp Ser
        130                 135                 140
Pro Arg Pro Leu Glu Ala Thr Ala Pro Thr Ala Pro Gln Pro Pro Leu
145                 150                 155                 160
Leu Leu Leu Leu Leu Leu Pro Val Gly Leu Leu Leu Leu Ala Ala Ala
                165                 170                 175
Trp Cys Leu His Trp Gln Arg Thr Arg Arg Arg Thr Pro Arg Pro Gly
            180                 185                 190
Glu Gln Val Pro Pro Val Pro Ser Pro Gln Asp Leu Leu Leu Val Glu
            195                 200                 205
His
```

<210> SEQ ID NO 14
<211> LENGTH: 209
<212> TYPE: PRT
<213> ORGANISM: Homo sapiens

<400> SEQUENCE: 14

```
Thr Gln Asp Cys Ser Phe Gln His Ser Pro Ile Ser Ser Asp Phe Ala
 1               5                  10                  15
Val Lys Ile Arg Glu Leu Ser Asp Tyr Leu Leu Gln Asp Tyr Pro Val
            20                  25                  30
Thr Val Ala Ser Asn Leu Gln Asp Glu Glu Leu Cys Gly Gly Leu Trp
        35                  40                  45
Arg Leu Val Leu Ala Gln Arg Trp Met Glu Arg Leu Lys Thr Val Ala
    50                  55                  60
Gly Ser Lys Met Gln Gly Leu Leu Glu Arg Val Asn Thr Glu Ile His
65                  70                  75                  80
Phe Val Thr Glu Cys Ala Phe Gln Pro Pro Ser Cys Leu Arg Phe
                85                  90                  95
Val Gln Thr Asn Ile Ser Arg Leu Leu Gln Glu Thr Ser Glu Gln Leu
            100                 105                 110
Val Ala Leu Lys Pro Trp Ile Thr Arg Gln Asn Phe Ser Arg Cys Leu
            115                 120                 125
Glu Leu Gln Cys Gln Pro Asp Ser Ser Thr Leu Pro Pro Pro Trp Ser
        130                 135                 140
Pro Arg Pro Leu Glu Ala Thr Ala Pro Thr Ala Pro Gln Pro Pro Leu
145                 150                 155                 160
Leu Leu Leu Leu Leu Leu Pro Val Gly Leu Leu Leu Leu Ala Ala Ala
                165                 170                 175
Trp Cys Leu His Trp Gln Arg Thr Arg Arg Arg Thr Pro Arg Pro Gly
            180                 185                 190
Glu Gln Val Pro Pro Val Pro Ser Pro Gln Asp Leu Leu Leu Val Glu
            195                 200                 205
His
```

<210> SEQ ID NO 15
<211> LENGTH: 209
<212> TYPE: PRT
<213> ORGANISM: Homo sapiens

<400> SEQUENCE: 15

Thr Gln Asp Cys Ser Phe Gln His Ser Pro Ile Ser Ser Asp Phe Ala
1               5                   10                  15

Val Lys Ile Arg Glu Leu Ser Asp Tyr Leu Leu Gln Asp Tyr Pro Val
            20                  25                  30

Thr Val Ala Ser Asn Leu Gln Asp Glu Glu Leu Cys Gly Gly Leu Trp
        35                  40                  45

Arg Leu Val Leu Ala Gln Arg Trp Met Glu Arg Leu Lys Thr Val Ala
    50                  55                  60

Gly Ser Lys Met Gln Gly Leu Leu Glu Arg Val Asn Thr Glu Ile His
65                  70                  75                  80

Phe Val Thr Thr Cys Ala Phe Gln Pro Pro Ser Cys Leu Arg Phe
                85                  90                  95

Val Gln Thr Asn Ile Ser Arg Leu Leu Gln Glu Thr Ser Glu Gln Leu
            100                 105                 110

Val Ala Leu Lys Pro Trp Ile Thr Arg Gln Asn Phe Ser Arg Cys Leu
        115                 120                 125

Glu Leu Gln Cys Gln Pro Asp Ser Ser Thr Leu Pro Pro Pro Trp Ser
    130                 135                 140

Pro Arg Pro Leu Glu Ala Thr Ala Pro Thr Ala Pro Gln Pro Leu
145                 150                 155                 160

Leu Leu Leu Leu Leu Leu Pro Val Gly Leu Leu Leu Ala Ala Ala
                165                 170                 175

Trp Cys Leu His Trp Gln Arg Thr Arg Arg Thr Pro Arg Pro Gly
            180                 185                 190

Glu Gln Val Pro Pro Val Pro Ser Pro Gln Asp Leu Leu Leu Val Glu
        195                 200                 205

His

<210> SEQ ID NO 16
<211> LENGTH: 209
<212> TYPE: PRT
<213> ORGANISM: Homo sapiens

<400> SEQUENCE: 16

Thr Gln Asp Cys Ser Phe Gln His Ser Pro Ile Ser Ser Asp Phe Ala
1               5                   10                  15

Val Lys Ile Arg Glu Leu Ser Asp Tyr Leu Leu Gln Asp Tyr Pro Val
            20                  25                  30

Thr Val Ala Ser Asn Leu Gln Asp Glu Glu Leu Cys Gly Gly Leu Trp
        35                  40                  45

Arg Leu Val Leu Ala Gln Arg Trp Met Glu Arg Leu Lys Thr Val Ala
    50                  55                  60

Gly Ser Lys Met Gln Gly Leu Leu Glu Arg Val Asn Thr Glu Ile His
65                  70                  75                  80

Phe Val Thr Lys Cys Ala Phe Gln Pro Pro Ser Cys Leu Arg Phe
                85                  90                  95

Val Gln Thr Asn Ile Ser Arg Leu Leu Gln Glu Thr Ser Glu Gln Leu
            100                 105                 110

Val Ala Leu Lys Pro Arg Ile Thr Arg Gln Asn Phe Ser Arg Cys Leu
        115                 120                 125

Glu Leu Gln Cys Gln Pro Asp Ser Ser Thr Leu Pro Pro Pro Trp Ser
    130                 135                 140

```
Pro Arg Pro Leu Glu Ala Thr Ala Pro Thr Ala Pro Gln Pro Pro Leu
145                 150                 155                 160

Leu Leu Leu Leu Leu Leu Pro Val Gly Leu Leu Leu Ala Ala Ala
                165                 170                 175

Trp Cys Leu His Trp Gln Arg Thr Arg Arg Thr Pro Arg Pro Gly
            180                 185                 190

Glu Gln Val Pro Pro Val Pro Ser Pro Gln Asp Leu Leu Leu Val Glu
        195                 200                 205

His
```

<210> SEQ ID NO 17
<211> LENGTH: 209
<212> TYPE: PRT
<213> ORGANISM: Homo sapiens

<400> SEQUENCE: 17

```
Thr Gln Asp Cys Ser Phe Gln His Ser Pro Ile Ser Ser Asp Phe Ala
1               5                   10                  15

Val Lys Ile Arg Glu Leu Ser Asp Tyr Leu Leu Gln Asp Tyr Pro Val
            20                  25                  30

Thr Val Ala Ser Asn Leu Gln Asp Glu Glu Leu Cys Gly Gly Leu Trp
        35                  40                  45

Arg Leu Val Leu Ala Gln Arg Trp Met Glu Arg Leu Lys Thr Val Ala
    50                  55                  60

Gly Ser Lys Met Gln Gly Leu Leu Glu Arg Val Asn Thr Glu Ile His
65                  70                  75                  80

Phe Val Thr Lys Cys Ala Phe Gln Pro Pro Pro Ser Cys Leu Arg Phe
                85                  90                  95

Val Gln Thr Asn Ile Ser Arg Leu Leu Gln Glu Thr Ser Glu Gln Leu
            100                 105                 110

Val Ala Leu Lys Pro Trp Ile Thr Arg Arg Asn Phe Ser Arg Cys Leu
        115                 120                 125

Glu Leu Gln Cys Gln Pro Asp Ser Ser Thr Leu Pro Pro Pro Trp Ser
130                 135                 140

Pro Arg Pro Leu Glu Ala Thr Ala Pro Thr Ala Pro Gln Pro Pro Leu
145                 150                 155                 160

Leu Leu Leu Leu Leu Leu Pro Val Gly Leu Leu Leu Ala Ala Ala
                165                 170                 175

Trp Cys Leu His Trp Gln Arg Thr Arg Arg Thr Pro Arg Pro Gly
            180                 185                 190

Glu Gln Val Pro Pro Val Pro Ser Pro Gln Asp Leu Leu Leu Val Glu
        195                 200                 205

His
```

<210> SEQ ID NO 18
<211> LENGTH: 209
<212> TYPE: PRT
<213> ORGANISM: Homo sapiens

<400> SEQUENCE: 18

```
Thr Gln Asp Cys Ser Phe Gln His Ser Pro Ile Ser Ser Asp Phe Ala
1               5                   10                  15

Val Lys Ile Arg Glu Leu Ser Asp Tyr Leu Leu Gln Asp Tyr Pro Val
            20                  25                  30

Thr Val Ala Ser Asn Leu Gln Asp Glu Glu Leu Cys Gly Gly Leu Trp
        35                  40                  45
```

```
Arg Leu Val Leu Ala Gln Arg Trp Met Glu Arg Leu Lys Thr Val Ala
 50                  55                  60
Gly Ser Lys Met Gln Gly Leu Leu Glu Arg Val Asn Thr Glu Ile His
 65                  70                  75                  80
Phe Val Thr Lys Cys Ala Phe Gln Pro Pro Ser Cys Leu Arg Phe
                 85                  90                  95
Val Gln Thr Asn Ile Ser Arg Leu Leu Gln Glu Thr Ser Glu Gln Leu
                100                 105                 110
Val Ala Leu Lys Pro Trp Ile Thr Arg Gln Asn Phe Ser Arg Cys Leu
                115                 120                 125
Glu Leu Gln Cys Gln Pro Asp Ser Ser Thr Leu Pro Pro Pro Trp Ser
130                 135                 140
Pro Arg Pro Leu Glu Ala Thr Ala Pro Thr Ala Pro Gln Pro Pro Leu
145                 150                 155                 160
Leu Leu Leu Leu Leu Leu Pro Val Gly Leu Leu Leu Ala Ala Ala
                165                 170                 175
Trp Cys Leu His Trp Gln Arg Thr Arg Arg Thr Pro Arg Pro Gly
                180                 185                 190
Glu Gln Val Pro Pro Val Pro Ser Pro Gln Asp Leu Leu Leu Val Glu
                195                 200                 205
His
```

<210> SEQ ID NO 19
<211> LENGTH: 137
<212> TYPE: PRT
<213> ORGANISM: Murine

<400> SEQUENCE: 19

```
Thr Pro Asp Cys Tyr Phe Ser His Ser Pro Ile Ser Ser Asn Phe Lys
  1               5                  10                  15
Val Lys Phe Arg Glu Leu Thr Asp His Leu Leu Lys Asp Tyr Pro Val
                 20                  25                  30
Thr Val Ala Val Asn Leu Gln Asp Glu Lys His Cys Lys Ala Leu
             35                  40                  45
Trp Ser Leu Phe Leu Ala Gln Arg Trp Ile Glu Gln Leu Lys Thr Val
 50                  55                  60
Ala Gly Ser Lys Met Gln Thr Leu Leu Glu Asp Val Asn Thr Glu Ile
 65                  70                  75                  80
His Phe Val Thr Ser Cys Thr Phe Gln Pro Leu Pro Glu Cys Leu Arg
                 85                  90                  95
Phe Val Gln Thr Asn Ile Ser His Leu Leu Lys Asp Thr Cys Thr Gln
                100                 105                 110
Leu Leu Ala Leu Lys Pro Cys Ile Gly Lys Ala Cys Gln Asn Phe Ser
                115                 120                 125
Arg Cys Leu Glu Val Gln Cys Gln Pro
                130                 135
```

<210> SEQ ID NO 20
<211> LENGTH: 149
<212> TYPE: PRT
<213> ORGANISM: Homo sapiens

<400> SEQUENCE: 20

```
Glu Glu Val Ser Glu Tyr Cys Ser His Met Ile Gly Ser Gly His Leu
  1               5                  10                  15
```

-continued

```
Gln Ser Leu Gln Arg Leu Ile Asp Ser Gln Met Glu Thr Ser Cys Gln
            20                  25                  30

Ile Thr Phe Glu Phe Val Asp Gln Glu Gln Leu Lys Asp Pro Val Cys
            35                  40                  45

Tyr Leu Lys Lys Ala Phe Leu Leu Val Gln Asp Ile Met Glu Asp Thr
        50                  55                  60

Met Arg Phe Arg Asp Asn Thr Pro Asn Ala Ile Ala Ile Val Gln Leu
65                  70                  75                  80

Gln Glu Leu Ser Leu Arg Leu Lys Ser Cys Phe Thr Lys Asp Tyr Glu
                85                  90                  95

Glu His Asp Lys Ala Cys Val Arg Thr Phe Tyr Glu Thr Pro Leu Gln
            100                 105                 110

Leu Leu Glu Lys Val Lys Asn Val Phe Asn Glu Thr Lys Asn Leu Leu
        115                 120                 125

Asp Lys Asp Trp Asn Ile Phe Ser Lys Asn Cys Asn Asn Ser Phe Ala
    130                 135                 140

Glu Cys Ser Ser Gln
145
```

METHODS OF USING MUTANT FLT3-LIGAND POLYPEPTIDES TO INDUCE CELLULAR EXPANSION

This is a division of application Ser. No. 09/109,100, filed Jul. 2, 1998, now U.S. Pat. No. 6,291,661, which is incorporated by reference.

FIELD OF THE INVENTION

The invention relates to mutant polypeptides in which protein residues involved in receptor-ligand interactions have been altered, and nucleic acids encoding these polypeptides.

BACKGROUND OF THE INVENTION

Flt3 Ligand (flt3-L) is a protein that binds to a cell surface tyrosine kinase, flt3 Receptor (flt3). The human flt3 gene has been cloned, and encodes a protein belonging to a family of structurally related tyrosine kinase receptors that contain five extracellular immunoglobulin (Ig)-like domains and an intracellular tyrosine kinase domain (Small et al., *Proc. Natl. Acad. Sci.* 91:459–463 (1994)). While flt3 is expressed in a limited number of tissues, including human bone marrow, thymus, spleen, liver, and lymph nodes, flt3-L is widely expressed in human tissue (Brasel, et al., *Leukemia* 9:1212–1218 (1995); Lyman, et al., *Blood* 83:2795–2801 (1994)).

Structural studies have demonstrated that human flt3-L is a member of the four helix bundle protein family of cytokines. The human flt3-L gene encodes a 235 amino acid type I transmembrane protein consisting of four domains: an amino-terminal 26 residue signal peptide; a 156 residue extracellular domain; a 23 amino acid transmembrane domain; and a 30 residue cytoplasmic domain (Hannum et al., *Nature* 368:643–648 (1994); Lyman et al., *Cell* 75:1157–1167 (1993); Lyman et al., *Blood* 83:2795–2801 (1994)). The amino terminal 26 residue signal peptide is cleaved from the full length polypeptide to yield the mature protein. Soluble flt3-L, which is thought to be released into circulation from the cell membrane by protease cleavage (Lyman et al., *Oncogene* 10:147–149 (1995)), is a noncovalently linked dimer containing six cysteine residues that apparently form intramolecular disulfides. Flt3-L is similar in size and structure to other four-helix hematopoietic growth factors such as Stem Cell Factor (SCF; also known as mast cell growth factor, Steel Factor (SF), and kit ligand) and macrophage colony stimulating factor (M-CSF), also known as colony stimulating factor I (CSF I), which also bind to and activate tyrosine kinase receptors. Despite their structural similarities, however, these three growth factors have very little conserved primary sequence.

The nature of flt3-L binding to flt3 has not been fully characterized previously. Site-directed mutagenesis has been used to study the structure and function of proteins, when the region of the protein to be mutagenized is already defined. However, in the case of certain proteins, such as flt3-L, the region of interest in the protein, e.g., the region that binds to flt3, is not well defined. The cross reactivity of murine and human flt3-L for flt3 (Lyman et al., *Blood* 83:2795–2801 (1994)) precludes the potential of identifying residues of interest by swapping interspecies segments of polypeptide between these ligands. Comprehensive mutational studies of some of the other members of the four helix bundle protein family may not be applicable to flt3-L, because a number of these species are monomeric and bind class I hematopoietic receptors, whereas native flt3-L forms a dimer, and binds to and activates a class III tyrosine kinase receptor.

Studies of flt3-L function indicate that its binding to flt3 initiates a signaling event that regulates the proliferation and differentiation of multiple lineages of cells of the hematopoietic system (Hannum et al., *Nature* 368:643–648 (1994); Lyman et al., *Cell* 75:157–1167 (1993); for review see Lyman, *Int. J. Hemat.* 62:63–73 (1995)). In combination with other growth factors, flt3-L has potent synergistic proliferative effects on hematopoietic precursor or stem cells (Hannum et al., *Nature* 368:643–648 (1994); Jacobsen et al., *J. Exp. Med.* 181:1357–1363 (1995)). Flt3-L can also induce the proliferation of other cell types, including T cells, early B cells and erythroid cells (U.S. Pat. No. 5,554,512).

SCF and M-CSF also activate hematopoietic cells. M-CSF primarily activates cells of the monocyte-macrophage lineage, while SCF acts on a number of cell lineages in both the lymphoid and myeloid pathway, as well as on primitive hematopoietic cells. Unlike flt3-L, SCF also stimulates proliferation and activation of mast cells, which produce histamine and can cause anaphylactic reactions in vivo. Intravenous administration of SCF in mice results in a respiratory distress syndrome characterized by breathing difficulties believed to result from degranulation of mast cells in the lungs. In contrast, flt3-L does not induce respiratory distress in mice following the injection of a large intravenous dose. See Lyman, *Int. J. Hematol.* 62:63–73 (1995).

In addition to its ability to induce cellular proliferation, flt3-L can induce the differentiation of hematopoietic progenitor cells, i.e., $CD34^+$ bone marrow progenitors and stem cells, into other cell types, including myeloid precursor cells, monocytic cells, macrophages, B lymphocytes, natural killer (NK) cells and dendritic cells. Dendritic cells can be used to present antigens, including tumor and viral antigens, to naive T cells, and can also be used as vaccine adjuvants, i.e., facilitators of immune responses to vaccines. See, e.g., WO 97/12633. Previously, the use of dendritic cells as immunostimulatory agents or adjuvants was limited by the low frequency of dendritic cells in peripheral blood, the limited accessibility to lymphoid organs, and the terminal state of differentiation of dendritic cells. Since dendritic cells are antigen-presenting cells, an increase in the dendritic cell population in vivo could augment presentation of antigens including tumor, bacterial and viral antigens to T cells.

Flt3-L's ability to regulate the growth and differentiation of hematopoietic progenitor cells indicates that it would be clinically useful in treating hematopoietic disorders, including aplastic anemia and myelodysplasia. Flt3-L can also be used to enhance populations of certain cell types in patients undergoing allogeneic, syngeneic or autologous bone marrow transplantation procedures having cytoreductive effects. See U.S. Pat. No. 5,554,512. For example, the use of ionizing radiation or chemical toxins to treat neoplasia results in cytotoxic effects on normal as well as cancerous cells. These therapies can cause myelosuppression, i.e., damage to bone marrow cells that are the precursors of cells including lymphocytes, erythrocytes and platelets. Myelosuppression results in cytopenia, i.e., blood cell deficits, that increase the risk of infection and bleeding disorders. One approach to the treatment of cytopenias is the removal of hematopoietic cells from a patient prior to cytoreductive therapies, and infusion of the cells back into the patient after therapy, to restore hematopoietic cell function. Since flt3-L induces proliferation of hematopoietic cells, it can be used in vitro to expand the population removed from the patient, and the expanded cell population can then be administered to the patient. Because flt3-L will also induce hematopoietic progenitor cells to differentiate into NK cells and dendritic cells, it can be administered to patients in need of expanding their NK cell or dendritic cell subpopulations, and used in vitro, to induce differentiation of isolated hematopoietic cells into NK and dendritic cells, which can then be administered to a patient.

Flt3-L's ability to induce the proliferation or differentiation of certain cell types indicates that it has therapeutic significance for other conditions, including Acquired Immune Deficiency Syndrome (AIDS) and human immunodeficiency virus (HIV) infection, and cancers, including breast cancer, lymphoma, small cell lung cancer, multiple myeloma, neuroblastoma, leukemias, testicular cancer and ovarian cancer.

Since flt3-L is known to induce proliferation and differentiation of certain cell types, it would be advantageous to develop methods of increasing or decreasing flt3-L function for therapeutic applications. One method of accomplishing this goal would be to characterize the relationship of flt3-L with its receptor, flt3, to determine which regions of flt3-L are implicated in ligand binding and biological activity, to develop flt3-L mutants with increased or decreased activity. The characteristics of flt3-L-flt3 binding and the ascertainment of the residues necessary for the induction of the biological effects attributed to the binding of flt3-L to flt3 have not been defined previously. The derivation of mutant forms of flt3-L which either augment or decrease the biological activity of flt3-L would be useful in designing therapeutic strategies for modulation of flt3-L activity to treat a variety of pathological conditions.

SUMMARY OF THE INVENTION

The invention includes a screening method for identifying mutant polypeptides in which at least one amino acid residue of a protein involved in a receptor-ligand interaction has been altered; isolated mutant polypeptides identified using this method; nucleic acids encoding these mutant polypeptides; and methods of treatment involving administration of these mutant polypeptides and nucleic acids. The method of screening described herein to identify protein residues involved in receptor-ligand interaction has allowed the definition of regions of interaction between flt3 Ligand (flt3-L) and its cognate receptor (flt3), and the identification and isolation of flt3-L mutants with altered biological activity. Using this information, polypeptides having multiple amino acid substitutions relative to the wild type human flt3-L have been constructed. The flt3-L mutant polypeptides and nucleic acids described herein are useful for in vitro applications, as well as therapeutically in vivo.

The invention includes a substantially pure flt3-L mutant protein or polypeptide. Flt3-L mutant polypeptides are preferably derived from a mammal, such as a mouse or a human.

The terms "protein" and "polypeptide" are used interchangeably herein, and refer to any chain of amino acids, regardless of length or post-translational modification (e.g., glycosylation or phosphorylation). Proteins or polypeptides of the invention are preferably at least 5 amino acids in length.

The full-length, wild type human flt3-L polypeptide sequence is disclosed in U.S. Pat. No. 5,554,512, and is set forth herein as SEQ ID NO:1. Amino acids one to twenty-six are cleaved from the full length protein to give the mature flt3-L protein, starting at the threonine residue at position 27 of the full length wild type protein. The sequence of the mature human wild type flt3-L polypeptide is set forth as SEQ ID NO:18. A "mutant flt3-L polypeptide" is a polypeptide having a sequence that has at least one difference in amino acid sequence relative to a wild type flt3-L polypeptide. Such a difference in amino acid sequence may arise, e.g., by substitution of one amino acid for another, or by deletion or addition of amino acids. These differences in amino acid sequence occur, e.g., within the regions encompassed by positions 8–15, 81–87 and 116–124 of the mature wild type human flt3-L protein (SEQ ID NO:18), and include proteins that differ from the mature wild type human flt3-L protein (SEQ ID NO:18) by amino acid substitutions at position 8, 84, 118 or 122.

Other mutant flt3-L polypeptides differ from wild type human flt3-L by amino acid substitutions that affect the dimerization interface of the protein. Such substitutions are at, e.g., positions 26, 27 or 64 of the mature wild type flt3-L polypeptide (SEQ ID NO:18). The "dimerization interface" of a protein includes those regions of the protein that physically contact each other when the protein is in its wild type dimeric form. Mutant flt3-L polypeptides also include flt3-L mutant ligands in which amino acid substitutions occur in regions outside of the mature protein. Such substitutions include, e.g., a substitution at the -3 position of the mature wild type human flt3-L polypeptide, i.e., at position 24 of the full length wild type human flt3-L (SEQ ID NO:1).

Mutant flt3-L polypeptides also include those having an altered charge distribution from a wild type flt3-L polypeptide. Such an altered charge distribution can result in altered flt3-L biological activity. For example, substitution of amino acid residues in the region of amino acid positions 118–124 of the mature flt3-L polypeptide (SEQ ID NO:18), e.g., at positions 118 or 122 of the mature flt3-L protein, with basic residues can produce a flt3-L mutant polypeptide with increased flt3-L biological activity. Basic residues can also be added to a wild type flt3-L polypeptide to produce a mutant flt3-L polypeptide with altered biological activity. Substitution of a basic residue in the region of position 81–87 of mature wild type flt3-L, e.g., substitution of the lysine residue at position 84 of the mature wild type protein, or an increase in net negative charge relative to wild type flt3-L, can also result in a flt3-L polypeptide with increased biological activity.

Mutant flt3-L polypeptides can be identified by, e.g., using the screening assay described herein. Once identified, the mutant polypeptides can be generated by conventional methods, e.g., techniques such as site-directed mutagenesis of appropriate nucleic acid sequences and expression of the mutant proteins in standard expression systems.

Mutant flt3-L polypeptides include "multiple mutant flt3-L polypeptides," i.e., flt3-L mutant polypeptides having more than one difference in amino acid sequence relative to a wild type flt3-L polypeptide. For example, a multiple mutant flt3-L polypeptide has two or more amino acid substitutions relative to the wild type human flt3-L polypeptide. Multiple mutant flt3-L polypeptides can be generated by, e.g., subcloning nucleic acid fragments containing appropriate mutations, or by site-directed mutagenesis of appropriate nucleic acid sequences, and expression of the mutant protein in a standard expression system. Multiple mutant flt3-L polypeptides include those having mutations affecting the dimerization interface as well as mutations affecting receptor binding affinity or induction of cellular proliferation or differentiation.

A "substantially identical" polypeptide sequence differs from a given sequence only by conservative amino acid substitutions or by one or more nonconservative substitutions, deletions, or insertions located at positions which do not destroy the biological activity of the polypeptide.

A "substantially pure" preparation is at least 60% by weight of the compound of interest, e.g., a flt3-L mutant polypeptide. Preferably the preparation is at least 75%, more preferably at least 90%, and most preferably at least 95% of the compound of interest. Purity of the compound can be assessed by appropriate methods that are well known in the art, e.g., column chromatography, polyacrylamide gel electrophoresis, or High Performance Liquid Chromatography (HPLC).

Polypeptides of the invention include, but are not limited to, recombinant polypeptides, natural polypeptides, and synthetic polypeptides, as well as preproteins or proproteins.

Polypeptides of the invention include those that have been modified to facilitate their uptake by cells, e.g., by packing into liposomes.

A polypeptide of the invention also includes those that have been physically linked to another polypeptide, e.g., a marker polypeptide. For example, the polypeptide is fused to a hexa-histidine tag to facilitate purification of bacterially expressed proteins, or a hemagglutinin tag to facilitate purification of proteins expressed in eukaryotic cells.

Soluble flt3-L mutant polypeptides are also included in the invention. These soluble polypeptides include those in which all or a part of the transmembrane portion of the polypeptide has been removed. The remainder of the protein may form a fusion protein with another soluble polypeptide or another cytokine such as erythropoietin (EPO), thrombopoietin (TPO), GM-CSF, G-CSF, members of the interleukin ("IL") family, e.g., IL-1, IL-2, IL-3, IL-4, IL-5, IL-6, IL-7, IL-8, IL-9, IL-10, IL-11, IL-12, IL-13, IL-14, or IL-15, or a fragment thereof. Alternatively, the other soluble polypeptide is an immunoglobulin Fc domain. Such fusion proteins are readily purified using a protein A column.

A "biologically active" polypeptide of the invention possesses any biological activity characteristic of flt3-L. Biological activities characteristic of flt3-L, include, but are not limited to, being capable of binding flt3, or transducing a stimulatory signal to a cell through membrane-bound flt3, resulting in effects such as cellular proliferation or differentiation.

A mutant flt3-L polypeptide exhibits increased or decreased flt3-L biological activity relative to a wild type flt3-L polypeptide.

"Increased" flt3-L biological activity is characterized by an increase of at least about 40% of a biological activity of wild type flt3-L, such as receptor binding affinity or induction of cellular proliferation or differentiation. Such an increase in biological activity can be measured using conventional techniques.

"Decreased" flt3-L biological activity is characterized by a decrease of at least about 40% of a biological activity of wild type flt3-L, such as receptor binding affinity or induction of cellular proliferation or differentiation. Such a decrease in biological activity can be measured using conventional techniques.

Another embodiment of the invention is a purified polynucleic acid that comprises a sequence encoding a flt3-L mutant polypeptide, a soluble flt3-L mutant polypeptide, or a fragment of such a polypeptide. Preferably, the nucleic acids are derived from a mammal. The sequence of a wild type human flt3-L cDNA is disclosed in U.S. Pat. No. 5,554,512, and is set forth herein as SEQ ID NO:2. A "flt3-L mutant nucleic acid" is a polynucleic acid encoding a flt3-L mutant polypeptide or protein, as described above. Such mutant flt3-L nucleic acids have undergone one or more insertions, deletions, substitutions or other mutations, or combinations thereof, relative to a wild type flt3-L polynucleic acid. Flt3-L mutant nucleic acids include "flt3-L multiple mutant nucleic acids" i.e., a polynucleic acid encoding flt3-L multiple mutant polypeptides, as described above.

The term "nucleic acid" encompasses both RNA and DNA, including cDNA, genomic DNA and synthetic (e.g., chemically synthesized) DNA. The nucleic acid is double-stranded or single-stranded. Where single-stranded, the nucleic acid is the sense strand or the antisense strand. Polynucleic acids of the invention include a recombinant nucleic acid incorporated into a vector, such as an autonomously replicating plasmid or virus; a cDNA or genomic DNA fragment produced by polymerase chain reaction (PCR) or restriction endonuclease treatment; or recombinant DNA that is part of a hybrid gene encoding additional polypeptide sequences.

An "isolated" molecule, such as a polypeptide or a nucleic acid, is free from association with at least some proteins that the respective native molecules are associated with in their natural environment. For example, an isolated polypeptide may be a purification product of a recombinant host cell culture, or a purified extract.

The invention also includes transfected or transformed cells harboring a nucleic acid described herein. Vectors and plasmids that include a nucleic acid properly positioned for expression are also within the invention.

A "transfected cell" or "transformed cell" is a cell into which (or into an ancestor of which) a nucleic acid of the invention has been introduced.

"Positioned for expression" means that the selected nucleic acid molecule is positioned adjacent to one or more sequence elements which direct transcription or translation of the sequence of the selected nucleic acid (i.e., the selected nucleic acid is operably associated with the sequence elements).

The flt3-L mutant proteins, including soluble mutant and multiple mutant flt3-L proteins, and nucleic acids of the invention are used to prepare pharmaceutical compositions to be used in methods of allogeneic, syngeneic or autologous transplantation. Pharmaceutical compositions comprise flt3-L mutant proteins or nucleic acids alone, or in combination with other growth factors or nucleic acids encoding such growth factors. Growth factors used with flt3-L include, but are not limited to, interleukins, colony stimulating factors and protein kinases.

The invention also includes a method of inducing proliferation of hematopoietic progenitor or stem cells using flt3-L mutant or multiple mutant proteins. The method includes the steps of isolating a population of cells to be expanded and exposing them in vitro to a mutant flt3-L polypeptide. The expanded cell population is then introduced into a patient. The population of cells is, for example, hematopoietic cells.

A method of expanding a population of cells in vivo is also included in the invention. According to the method, a pharmaceutical composition of a mutant or multiple mutant flt3-L polypeptide or nucleic acid sufficient to induce proliferation of a target cell population is administered to a patient.

The invention also includes a method of modulating an immune response in a subject, by administering to the subject a therapeutically effective amount of a pharmaceutical composition that includes a flt3-L mutant polypeptide or nucleic acid.

The invention further includes a method of treating an immune disorder in a patient by administration of a therapeutically effective amount of a pharmaceutical composition comprising a flt3-L mutant polypeptide or nucleic acid. Such immune disorders include, but are not limited to, allergy, immunosuppression, and autoimmunity.

A method of treating a pathological condition by administration of a pharmaceutical composition of a flt3-L mutant polypeptide or nucleic acid is also included in the invention. Such pathological conditions include, but are not limited to, myelodysplasia, aplastic anemia, HIV infection and cancer, including breast cancer, lymphoma, small cell lung cancer, multiple myeloma, neuroblastoma, acute leukemia, testicular cancer and ovarian cancer.

The invention also includes a method of inducing cellular differentiation by exposure to flt3-L mutant polypeptides and nucleic acids. The method includes the steps of isolating a target population of cells and administering an amount of flt3-L mutant polypeptide sufficient to induce the production of differentiated cells. The target population of cells is, e.g., hematopoietic cells, and the differentiated cells are, e.g., Natural Killer (NK), dendritic cells or facilitating cells. Populations of differentiated cells are then introduced into a subject in need of such cells. Alternatively, the method involves the in vivo administration of flt3-L mutant or multiple mutant polypeptides to a patient.

Induction of "cellular differentiation" is the induction of cells to differentiate along certain lineages. For example, hematopoietic cells can differentiate into cell types including NK cells, dendritic cells, and facilitating cells.

The invention also includes a method of augmenting an immune response in a patient, by administering an amount of a flt3-L mutant polypeptide sufficient to generate an increase in the number of the patient's dendritic cells. The patient can have an infectious disease, such as HIV, or a cancerous neoplastic disease.

A method of enhancing a mammal's immune response to a vaccine antigen is also included in the invention. The method includes the steps of administering an immunogenic amount of the vaccine antigen and an immunogenicity-augmenting amount of a flt3-L mutant polypeptide, in concurrent or sequential combination with the vaccine antigen.

An "adjuvant" is a substance that enhances, augments or potentiates a host's immune response to a vaccine antigen. "Immunogenicity" is the ability of an immunogen or antigen to provoke an immune response in a subject.

A "therapeutically effective amount" of a substance is an amount capable of producing a medically desirable effect in a treated subject.

The invention also includes a screening method for identifying residues involved in receptor binding in a receptor-ligand system. The method includes the steps of:

subjecting a nucleic acid population encoding the ligand to random mutagenesis, to form a mutagenized ligand population;

transforming cells with the mutagenized ligand population, to form transformed colonies;

transferring the transformed colonies to a first membrane;

overlaying the first membrane with a second membrane, the second membrane being coated with capture means for capturing the ligand and mutants thereof;

reacting the second membrane with a receptor for the ligand; and subsequently reacting the second membrane with detection means for detecting receptor binding to the ligand or mutants thereof.

The transformed cells can be, e.g., yeast or bacterial cells.

The invention also includes a method of screening to identify mutant polypeptides with altered expression characteristics. This method includes the steps of:

subjecting a nucleic acid population encoding the ligand to mutagenesis, to form a mutagenized ligand population;

transforming cells with the mutagenized ligand population, to form transformed colonies;

transferring the transformed colonies to a first membrane;

overlaying the first membrane with a second membrane, the second membrane being coated with capture means for capturing the ligand and mutants thereof;

reacting the second membrane with a receptor for the ligand; and subsequently reacting the second membrane with means for detecting receptor binding to the ligand or mutants thereof.

The transformed cells can be, e.g., yeast or bacterial cells.

A "receptor-ligand system" is a system in which a ligand binds to a receptor that specifically recognizes it. As used herein, "capture means" include any means that can be used for capturing a specific ligand. Such capture means include, for example, an antibody that specifically recognizes and binds a particular ligand. "Detection means" include any means that can be used for the detection of receptor-ligand binding. Such detection means include, for example, an antibody that specifically recognizes and binds a particular receptor bound to an immobilized ligand, and fluorescent or enzymatic means to detect the bound receptor.

The invention also includes mutant M-CSF and SCF polypeptides, and nucleic acids encoding them. Such mutant polypeptides have sequences with at least one difference in amino acid sequence from their wild type counterparts, in regions that correspond to key positions involved in receptor-ligand binding. These regions include the regions corresponding to the regions defined by amino acid positions 8–15, 81–87 and 116–124 of the mature human wild type flt3-L polypeptide when the amino acid sequences of flt3-L, SCF and M-CSF are aligned. For example, such mutants include those in which there is an amino acid difference at the position corresponding to position 8 in mature wild type flt3-L, e.g., position 9 of M-CSF.

The mutant SCF and M-CSF polypeptides include those with amino acid differences that cause the mutant polypeptides to lose affinity for their receptors, and instead bind a different receptor. For example, the invention includes a mutant SCF polypeptide which binds to and activates flt3-expressing cells, but which does not bind c-kit.

The invention further includes small molecules in which the key residues involved in flt3 binding, as defined herein, or functional groups corresponding to the side chains of these residues, have been inserted. Such residues include, e.g., those within the regions defined by amino acid positions 8–15, 81–87 and 116–124, and amino acid positions 26, 27 and 64, of the mature human flt3-L wild type polypeptide. Functional groups which correspond to the side chains of amino acids are well known to those in the art and include, e.g., substitution of an amine functional group for a lysine residue. A "small molecule" is a molecule that acts as a scaffold by maintaining a three dimensional structure allowing flt3-L binding to and activation of flt3-expressing cells.

Additional objects and advantages of the invention will be set forth in part in the description that follows, and in part will be apparent from the description, or may be realized during the practice of the invention. The objects and advantages of the invention will be realized and attained by means of the elements and combinations particularly pointed out in the appended claims. Both the foregoing general description and the following detailed description are exemplary and explanatory only, and are not restrictive of the claimed invention. All publications, patent applications and other references mentioned herein are incorporated by reference in their entirety.

BRIEF DESCRIPTION OF THE DRAWINGS

FIG. 1 is an amino acid sequence alignment of the human and murine flt3 Ligand polypeptide (flt3-L) with the human M-CSF polypeptide.

DETAILED DESCRIPTION

Figure 2:
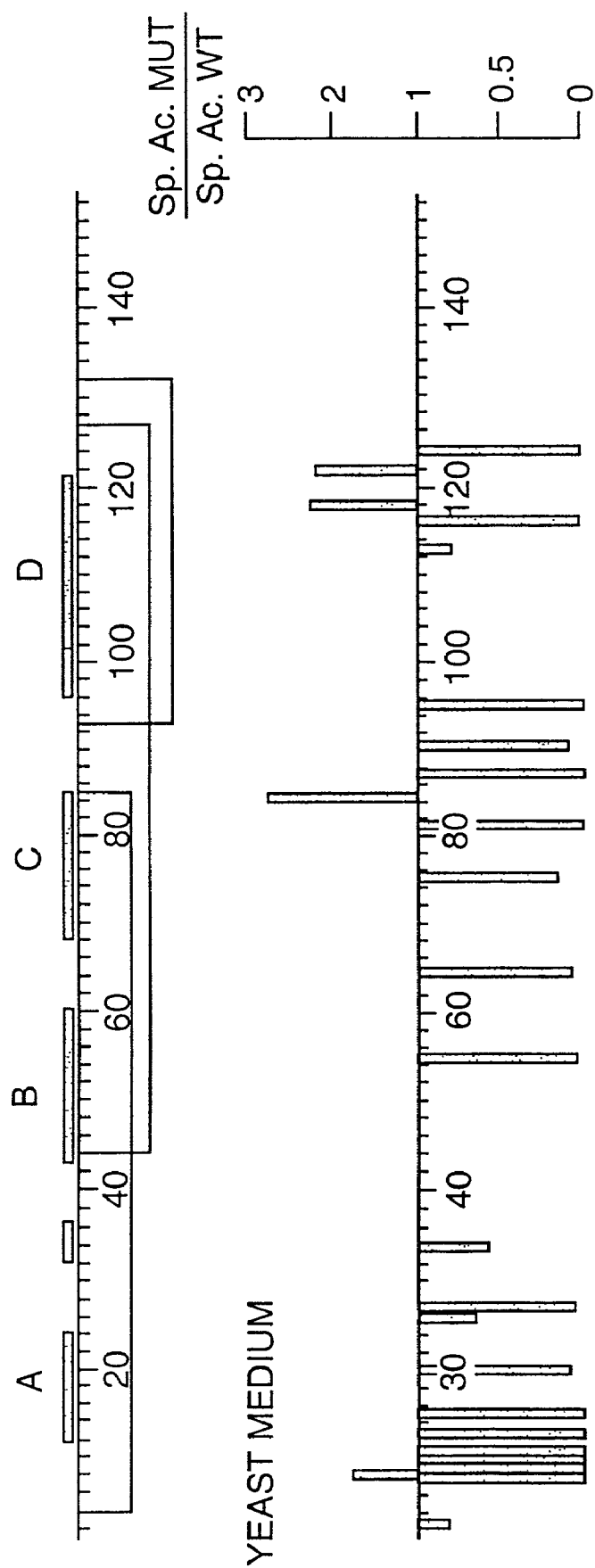
FIG. 2 is a representation of the secondary (top) and primary (bottom) structures of flt3-L, showing the specific activity of isolated flt3-L mutant polypeptides relative to the wild type flt3-L polypeptide.

Flt3-L mutant polypeptides, including multiple mutant polypeptides, having altered biological activity have been identified and isolated. In addition, novel mutants have been constructed that exhibit increased or decreased flt3-L biological activity. The flt3-L mutants described herein can be used in vitro, or in vivo, in pharmaceutical compositions, to modulate the effects of flt3-L-flt3 binding to treat a variety of pathological conditions. In addition, the method used to identify these mutants is applicable to any ligand-receptor system for which appropriate biological assays can be derived.

To identify flt3-L mutants, yeast colonies were transformed with DNA encoding wild type flt3-L that had been randomly mutagenized. The transformed colonies were lifted onto a first membrane, which was overlaid by a second or "capture" membrane. The second membrane was coated with an antibody to the ligand, to form a membrane "sandwich." Ligand protein secreted by the yeast passed through the first membrane, and was captured by the antibody immobilized on the second membrane. The second membrane was then probed with the receptor for the ligand, and means were used to detect receptor-ligand binding.

This method was used to screen a randomly mutagenized ligand, flt3-L, to identify the residues involved in binding to its receptor, flt3. Sixty thousand colonies were screened, and DNA from a subset of 59 clones was sequenced. Thirty-one single amino acid substitutions at 24 positions throughout the primary sequence of flt3-L either enhanced or reduced activity in receptor binding and cell proliferation assays. Representative flt3-L mutant proteins were purified and analyzed for receptor binding, specific activity, Stokes radius and helical content.

A structural model of wild type flt3-L was generated by aligning its sequence with that of M-CSF, a member of the four-helix bundle protein family (FIG. 1), and using the x-ray structure of M-CSF as a model. The model, which predicts that flt3-L is a dimer, has allowed the grouping of mutations identified using the screening method. Two types of mutants were identified, those that are directly involved in flt3-flt3-L binding, and those that are not directly involved in the binding interaction. While amino acid substitutions that alter flt3-L activity were found at sites that are scattered throughout the primary flt3-L sequence, most of these sites were tightly grouped when displayed on the structural model of flt3-L. The residues of flt3-L implicated in receptor binding map to a patch of the molecule defined by a region encompassing the amino terminus of the molecule and the amino-terminal portion of helix A, the C terminus of helix C, the C terminus of helix D and the disulfide-constrained loop that is C-terminal to helix D. Thus, the method described herein has allowed identification of the key residues involved in flt3 binding.

Other mutants were identified that were not directly involved in receptor binding. These mutants had an altered structure or charge distribution from that of wild type flt3-L. For example, the structural model of flt3-L predicts that the protein is dimeric form, and mutants were identified which interfered with the predicted dimerization interface, resulting in a monomeric form of flt3-L. One of these mutants was expressed at a high level, but had low affinity for flt3. Flt3-L mutant polypeptides having both mutations that affect dimerization and mutations that increase the affinity of flt3-L for flt3 can be constructed using methods described herein. Such mutants would result in flt3-L mutant polypeptides which bind to but do not crosslink cell surface flt3 molecules. Since crosslinking is crucial to cellular activation, these combined mutants can act as antagonists. Such antagonists can be used, for example, for the treatment of acute myelogenous leukemias (AMLs), which express flt3.

Mutants were also identified in which an additional positive charge due to an amino acid substitution resulted in a flt3-L mutant polypeptide with an increased binding affinity for flt3. Mutant flt3-L polypeptides with increased binding affinity and biological activity can therefore be designed by substitution of wild type flt3-L amino acid residues with basic residues, or addition of basic residues to wild type-flt3-L. Other mutants were identified in which substitution of a basic amino acid with another amino acid resulted in an increase in flt3-L biological activity. Therefore, mutant flt3-L polypeptides in which a basic amino acid has been substituted with another amino acid, and which have increased biological activity, can be designed using the methods described herein.

As described herein, mutations reducing flt3-L biological activity occur throughout the primary sequence of the molecule, and different amino acid changes at the same position can either decrease or increase flt3-L biological activity, such as receptor binding or activity in cell proliferation assays. Seventeen independent isolates of the same flt3-L$^{++}$ mutation were obtained. These findings support the reliability of the screening method. The method can also be used to identify residues involved in binding in other receptor-ligand systems, and to generate mutants in those systems.

The screening method has allowed the identification of flt3-L mutant polypeptides that increase or decrease flt3-L biological activity, such as flt3 binding or induction of proliferation of hematopoietic cells, T cells or erythrocytes. These flt3-L mutant polypeptides can be used in therapeutic methods designed to modulate in vivo flt3-L activity. Flt3-L mutants can also be used to expand or differentiate cell populations in vitro or in vivo. Cells expanded in vitro may be transplanted into a patient in need of such cells, e.g., patients who have undergone therapies that have cytoreductive effects. Bone-marrow progenitor cells may be induced by addition of mutant flt3-L to differentiate into dendritic cells, e.g., which may be used as vaccine adjuvants. Flt3-L mutants may be used to treat pathological conditions including myelodysplasia, aplastic anemia, HIV infection, immunosuppression, autoimmune disorders, allergy and malignancies, including leukemias.

In addition, since the method described herein has allowed identification of the key residues involved in flt3-flt3-L interaction, corresponding residues can be altered in structurally related proteins, which can be used therapeutically. For example, flt3-L shares a high degree of structural similarity to the growth factors SCF and M-CSF. Regions of these proteins corresponding to the key residues in flt3 binding can be mutated to alter receptor specificity, so that, for example, these proteins activate the same cell types as flt3-L. The key residues for flt3 binding as identified herein, or functional groups corresponding to the side chains of these residues, can also be engrafted onto small molecules. An example of a functional group that can be used is an amine functional group, which can be used to replace a lysine residue. These small molecules maintain a three-dimensional structure that allows binding to and activation of flt3-expressing cells.

Flt3-L Mutant Polypeptides and Nucleic Acids

Flt3-L mutant polypeptides exhibit increased or decreased biological activity relative to wild type flt3-L polypeptide. These mutant polypeptides, which include multiple mutant polypeptides, have at least 40% of a biological activity of wild type flt3-L, such as receptor binding or induction of cellular proliferation or differentiation. Alternatively, the mutant polypeptides exhibit a decrease of 40% or more of a biological activity of wild type flt3-L polypeptide. Such comparisons are generally based on equal concentrations of the molecules being compared. The comparison can also be based on the amount of protein or polypeptide required to reach 50% of the maximal stimulation obtainable.

Another aspect of the invention is soluble flt3-L mutant polypeptides. These polypeptides lack the transmembrane region that would cause retention of the polypeptide on the cell membrane. Soluble flt3-L mutant polypeptides include those that comprise a native or heterologous signal peptide when initially synthesized to promote secretion. The signal peptide is cleaved upon secretion of the flt3-L mutant polypeptide from the cell. The soluble flt3-L mutant polypeptides retain the ability to bind flt3. Soluble flt3-L mutant polypeptides can also include the transmembrane region or part of the cytoplasmic domain or other sequences, provided that the soluble flt3-L protein can be secreted.

Soluble flt3-L mutant polypeptides are identified and distinguished from their non-soluble membrane-bound counterparts by separating intact cells which express the desired protein from the culture medium, e.g., by centrifugation, and assaying the culture supernatant for the presence of the desired protein.

Soluble forms of flt3-L mutant polypeptides can be easily purified, since the soluble proteins are secreted from the cells. Further, soluble proteins are suitable for intravenous administration.

The soluble flt3-L mutant polypeptides of the invention include those comprising a substantial portion of the extracellular domain of a native, full length flt3-L protein. For example, a soluble flt3-L mutant polypeptide may comprise amino acids 28 through 235 of SEQ ID NO:1. In addition, truncated soluble flt3-L mutant proteins comprising less than the entire extracellular domain of native flt3-L are included in the invention. Such truncated soluble proteins are represented by the sequence of amino acids 28–160, 28–182 or 28–185 of the full length flt3-L human polypeptide, i.e., SEQ ID NO:1. Soluble flt3-L mutant polypeptides include those comprising a heterologous signal peptide that functions within specific host cells to allow protein expression, or the native flt3-L signal peptide.

Also within the invention are fusion proteins in which a portion of a mutant flt3-L polypeptide is fused to an unrelated protein or polypeptide (i.e., a fusion partner). The fusion partners include moieties selected to facilitate purification, detection, or solubilization, or to provide some other function, such as another cytokine, interleukin or tyrosine kinase. Fusion proteins include those produced by expressing a hybrid gene in which a nucleotide sequence encoding all or a portion of flt3-L is joined in-frame to a nucleotide sequence encoding the fusion partner. Fusion partners include, but are not limited to, the constant region (Fc) of an immunoglobulin, such as IgG; colony stimulating factors, such as GM-CSF and G-CSF; the interleukins, including IL-1, -2, -3, -4, -5, -6, -7, -8, -9, -10, -11, -12, -13, -14, -15, -16, -17 or -18; EPO; and TPO. Fusion of the Fc portion of IgG to a flt3-L mutant polypeptide increases its stability and half life. Fusion proteins include those comprising the yeast a factor signal peptide, a FLAG® peptide such as those described in U.S. Pat. No. 5,011,912, and a portion of a soluble flt3-L mutant polypeptide corresponding to the region encompassed by amino acids 28 to 235 of SEQ ID NO:1. Recombinant fusion proteins are expressed in and secreted from, e.g., yeast cells. The FLAG® peptide facilitates purification of the protein. Bovine mucosal enterokinase is used to cleave the FLAG® peptide from the soluble flt3-L mutant polypeptide.

Flt3-L mutant polypeptide fusions comprise peptides added to facilitate purification and identification. Such peptides include, for example, poly-His or the antigenic identification peptides described in U.S. Pat. No. 5,011,912 and in Hopp et al., *Bio/Technology* 6:1204 (1988).

The invention further includes flt3-L mutant polypeptides with or without associated native-pattern glycosylation. Mutant flt3-L polypeptides expressed in yeast or mammalian cells (e.g., COS-7 cells) are similar to or significantly different from a native flt3-L polypeptide in molecular weight and glycosylation pattern, depending upon the choice of expression system. Expression of flt3-L polypeptides in bacterial cells, such as *E. coli*, results in non-glycosylated molecules.

Flt3-L mutant polypeptides can be modified by forming covalent or aggregative conjugates with other chemical moieties, such as glycosyl groups, lipids, phosphate, acetyl groups and the like. Covalent derivatives of flt3-L mutant polypeptides are prepared, e.g., by linking the chemical moieties to functional groups on flt3-L amino acid side chains or at the amino terminus or carboxy terminus of a flt3-L mutant polypeptide or the extracellular domain thereof. Other derivatives include covalent or aggregative conjugates of a flt3-L mutant polypeptide or its fragments with other proteins or polypeptides, such as by synthesis in recombinant culture as amino terminal or carboxy terminal fusions proteins. For example, the conjugate comprises a signal or leader polypeptide sequence (e.g., the α-factor leader of *Saccharomyces*) at the amino terminus of a flt3-L mutant polypeptide. The signal or leader peptide co-translationally or post-translationally directs transfer of the conjugate from its site of synthesis to a site inside or outside of the cell membrane or cell wall.

Isolated nucleic acids encoding soluble flt3-L mutant proteins are also included in the invention. Nucleic acids capable of expressing soluble mutant flt3-L polypeptides, including truncated polypeptides, are prepared by any of a number of conventional techniques. Techniques for preparation of recombinant nucleic acids and expression of polypeptides therefrom are described in detail in Sambrook, et al., *Molecular Cloning, A Laboratory Manual*, Cold Spring Harbor Press, Cold Spring Harbor, N.Y., 1989, and Ausubel et al., *Current Protocols in Molecular Biology*, John Wiley and Sons, New York, 1994. For example, desired nucleic acid sequences are chemically synthesized using known techniques or produced by restriction endonuclease digestion of full length cloned DNA sequences, and isolated by electrophoresis on agarose gels. Linkers containing restriction endonuclease cleavage sites can be employed to insert the desired DNA fragment into an expression vector, or the fragment can be digested at cleavage sites naturally present therein. The polymerase chain reaction procedure also can be used to amplify a DNA sequence encoding a desired protein fragment. See, e.g., *PCR Protocols, A Guide to Methods and Applications*, Academic Press, New York, 1990. Known mutagenesis techniques can be employed to insert a stop codon at a desired point, e.g., immediately downstream of the codon for the last amino acid of the extracellular domain. In another approach, enzymatic treatment (e.g., using Bal 31 exonuclease) can be employed to delete terminal nucleotides from a DNA fragment to obtain a fragment having a particular desired terminus. Linkers that can be ligated to the blunt ends produced by Bal 31 digestion and that contain restriction endonuclease cleavage sites are commercially available. Oligonucleotides that reconstruct the amino or carboxy terminus of a DNA fragment to a desired point can be synthesized and ligated to the DNA fragment. The synthesized oligonucleotides include those containing a restriction endonuclease cleavage site upstream of the desired coding sequence and position an initiation codon (ATG) at the amino-terminus of the coding sequence.

Constructs that encode mutant flt3-L polypeptides having various additions or substitutions of amino acid residues or sequences, or deletions of terminal or internal residues or sequences in addition to those affecting flt3-L biological activity, are also included in the invention. For example, N-glycosylation sites in the flt3-L extracellular domain can be modified to preclude glycosylation, allowing expression of a reduced carbohydrate analog in mammalian and yeast expression systems. N-glycosylation sites in eukaryotic polypeptides are characterized by the amino acid triplet Asn-X-Y, wherein X is any amino acid except Pro, and Y is Ser or Thr. The human flt3-L protein has two such triplets, at amino acids 126–128 and 150–152 of SEQ ID NO:1. Appropriate substitutions, additions or deletions to the nucleotide sequence encoding these triplets result in prevention of attachment of carbohydrate residues at the Asn side chain. Alteration of a single nucleotide, chosen so that Asn is replaced by a different amino acid, for example, is sufficient to inactivate an N-glycosylation site. Known procedures for inactivating N-glycosylation sites in proteins include those described in U.S. Pat. No. 5,071,972 and EP 276,846.

Recombinant expression vectors containing a DNA encoding flt3-L mutant polypeptide can be prepared using known methods. The expression vectors include a flt3-L mutant DNA sequence operably linked to suitable transcriptional or translational regulatory nucleotide sequences, such as those derived from a mammalian, microbial, viral, or insect gene. Examples of regulatory sequences include transcriptional promoters, operators, or enhancers, an mRNA ribosomal binding site, and appropriate sequences which control transcription and translation initiation and termination. Nucleotide sequences are "operably linked" when the regulatory sequence functionally relates to the flt3-L mutant DNA sequence. Thus, a promoter nucleotide sequence is operably linked to a flt3-L mutant DNA sequence if the promoter nucleotide sequence controls the transcription of the flt3-L mutant DNA sequence. An origin of replication, or equivalent means for replicating in particular host cells, and selection genes are used to identify transformants.

Suitable host cells for expression of flt3-L polypeptides include prokaryotes, yeast or higher eukaryotic cells. Appropriate cloning and expression vectors for use with bacterial, fungal, yeast, and mammalian cellular hosts are described, for example, in Pouwels et al., *Cloning Vectors: A Laboratory Manual*, Elsevier, N.Y. 1985. Cell-free translation systems are also appropriate for producing flt3-L mutant polypeptides using RNAs derived from DNA constructs disclosed herein.

Suitable prokaryotic hosts include gram negative or gram positive organisms, for example, *E. coli, Bacillus subtilis, Salmonella typhimurium*, and various other species within the genera *Pseudomonas, Streptomyces, Bacillus* or *Staphylococcus*. A mutant flt3-L polypeptide may include an amino terminal methionine residue to facilitate expression of the recombinant polypeptide in the prokaryotic host cell. The amino terminal methionine may be cleaved from the expressed recombinant flt3-L mutant polypeptide.

Expression vectors for use in prokaryotic host cells generally comprise one or more phenotypic selectable marker genes. A phenotypic selectable marker gene is, for example, a gene encoding a protein that confers antibiotic resistance or supplies an autotrophic requirement. Examples of useful expression vectors for prokaryotic host cells include those derived from commercially available plasmids such as the cloning vector pBR322 (ATCC 37017). pBR322 contains genes for ampicillin and tetracycline resistance, and thus provides a simple means for identifying transformed cells. To construct an expression vector using pBR322, an appropriate promoter and a flt3-L mutant DNA sequence are inserted into the pBR322 vector. Other commercially available vectors include, for example, pKK223-3 (Pharmacia Fine Chemicals, Uppsala, Sweden) and PGEMI (Promega Biotec, Madison, Wis., USA).

Promoter sequences used in recombinant prokaryotic host cell expression vectors include β-lactamase (penicillinase), lactose promoter system (Chang et al., *Nature* 275:615 (1978); and Goeddel et al., *Nature* 281:544 (1979)), tryptophan (trp) promoter system (Goeddel et al., *Nucl. Acids Res.* 8:4057 (1980); and EP-A- 36776) and tac promoter (Sambrook et al., *Molecular Cloning, A Laboratory Manual*, Cold Spring Harbor Press, Cold Spring Harbor, N.Y., 1982, at 412). A particularly useful prokaryotic host cell expression system employs a phage $\lambda_L$ promoter and a cI857ts thermolabile repressor sequence. Plasmid vectors which incorporate derivatives of the $\lambda P_L$ promoter are available from the American Type Culture Collection (ATCC). These vectors include plasmid pHUB2 (resident in *E. coli* strain JMB9 (ATCC 37092)) and pPLc28 (resident in *E. coli* RRI (ATCC 53082)).

Flt3-L mutant polypeptides include those expressed in yeast host cells, preferably from the genus *Saccharomyces* (e.g., *S. cerevisiae*). Other genera of yeast, which can be used include *Pichia, K. lactis* or *Kluyveromyces*. Yeast vectors containing an origin of replication sequence from a 2µ yeast plasmid, an autonomously replicating sequence (ARS), a promoter region, sequences for polyadenylation, sequences for transcription termination, and a selectable marker gene can also be used. Suitable promoter sequences for yeast vectors include, among others, promoters for metal-lothionein, 3-phosphoglycerate kinase (Hitzeman et al., *J. Biol. Chem.* 255:2073 (1980)) or other glycolytic enzymes (Hess et al., *J. Adv. Enzyme Reg.* 7:149 (1968); and Holland et al., *Biochem.* 17:4900 (1978)), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other suitable vectors and promoters for use in yeast expression are further described in Hitzeman, EPA-73,657; Fleer et. al., *Gene*, 107:285–195 (1991); and van den Berg et. al., *Bio/Technology*, 8:135–139 (1990). The glucose-repressible ADH2 promoter described by Russell et al. (*J. Biol. Chem.* 258:2674, (1982)) and Beier et al. (*Nature* 300:724, (1982)) is also suitable. Shuttle vectors that can replicate in both yeast and bacteria are constructed e.g., by inserting DNA sequences from pBR322 for selection and replication in, e.g., *E. coli* (e.g., the $Amp^r$ gene and origin of replication) into the above-described yeast vectors.

The yeast α-factor leader sequence directs secretion of mutant flt3-L polypeptides. The α-factor leader sequence can be inserted between the promoter sequence and the structural gene sequence. See, e.g., Kurjan et al., *Cell* 30:933 (1982); Bitter et al., *Proc. Natl. Acad Sci.* USA 81:5330 (1984) U.S. Pat. No. 4,546,082; and EP 324,274. Other leader sequences suitable for facilitating secretion of recombinant polypeptides from yeast hosts are known to those of skill in the art. Modification of a leader sequence near its 3' end, so that it contains one or more restriction sites, facilitates fusion of the leader sequence to the structural gene.

Yeast transformation protocols are known to those of skill in the art. One such protocol is described by Hinnen et al., *Proc. Natl. Acad. Sci.* USA 75:1929 (1978). This protocol selects for $Trp^+$ transformants in a selective medium, wherein the selective medium consists of 0.67% yeast nitrogen base, 0.5% casamino acids, 2% glucose, 10 μg/ml adenine and 20 μg/ml uracil.

Induction of expression in a "rich" medium can be carried out in yeast host cells transformed by vectors containing the ADH2 promoter sequence. An example of a rich medium is one consisting of 1% yeast extract, 2% peptone, and 1% glucose supplemented with 80 μg/ml adenine and 80 μg/ml uracil. Derepression of the ADH2 promoter occurs when glucose is exhausted from the medium.

Mammalian or insect host cell culture systems can also be employed to express recombinant flt3-L polypeptides. Baculovirus systems for production of heterologous proteins in insect cells are reviewed by Luckow and Summers, *Bio/Technology* 6:47 (1988). Established cell lines of mammalian origin are also used as host cells. Examples of suitable mammalian host cell lines include the COS-7 line of monkey kidney cells (ATCC CRL 1651) (Gluzman et al. *Cell* 23:175 (1981)), L cells, C127 cells, 373 cells (ATCC CCL 163), Chinese hamster ovary (CHO) cells, HeLa cells, and BHK (ATCC CRL 10) cell lines, and the CV-I/EBNA-1 cell line derived from the African green monkey kidney cell line CVI (ATCC CCL 70) as described by McMahan et al., *EMBO J.* 10:2821 (1991).

Transcriptional and translational control sequences for use mammalian host cell expression vectors can be excised from viral genomes. Useful promoter and enhancer sequences are derived from Polyoma virus, Adenovirus 2, Simian Virus 40 (SV40), and human cytomegalovirus. DNA sequences derived from the SV40 viral genome, for example, the SV40 origin, early and late promoter, enhancer, splice, and polyadenylation sites, can be used to express a structural gene sequence in a mammalian host cell. Viral early and late promoters are particularly useful because both are easily obtained from a viral genome as a fragment which may also contain a viral origin of replication (Fiers et al., *Nature* 273:113 (1978)). Smaller or larger SV40 fragments may also be used, provided the approximately 250 bp sequence extending from the Hind III site toward the Bgl I site located in the SV40 viral origin of replication site is included.

Exemplary expression vectors for use in mammalian host cells can be constructed as disclosed by Okayama et al. *Mol. Cell. Biol.* 3:280 (1983). A useful system for stable, high level expression of mammalian cDNAs in C127 murine mammary epithelial cells can be constructed substantially as described by Cosman et al. *Mol. Immunol.* 23:935 (1986). A useful high expression vector, PMLSV N1/N4, described by Cosman et al., *Nature* 312:768 (1984) is deposited as ATCC 39890. Additional useful mammalian expression vectors are described in EP-A- 0367566, and in U.S. patent application Ser. No. 07/701,415, filed May 16, 1991. Vectors derived from retroviruses are also suitable expression vectors.

Flt3-L mutant polypeptides include those produced by a recombinant expression system, or purified from cells as naturally occurring mutants. One process for producing a mutant flt3-L polypeptide comprises culturing a host cell transformed with an expression vector comprising a DNA sequence that encodes a mutant flt3-L polypeptide under conditions sufficient to promote its expression. Mutant flt3-L is then recovered from the culture medium or cell extracts, depending upon the expression system employed. Procedures for purifying a recombinant protein vary according to such factors as the type of host cells employed and whether or not the recombinant protein is secreted into the culture medium.

For example, when expression systems that secrete the recombinant protein are employed, the culture medium first may be concentrated using a commercially available protein concentration filter, for example, an Amicon or Millipore Pellicon ultrafiltration unit. Following the concentration step, the concentrate can be applied to a purification matrix such as a gel filtration medium. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Finally, one or more reversed-phase high performance liquid chromatography (RP-HPLC) steps employing hydrophobic RP-HPLC media, (e.g., silica gel having pendant methyl or other aliphatic groups) can be employed to further purify mutant flt3-L polypeptides. Some or all of the foregoing purification steps, in various combinations, are well known and can be employed to provide a substantially homogeneous recombinant protein.

Mutant flt3-L polypeptides can be affinity purified on columns comprising the ligand binding domain of flt3. The flt3-L mutant polypeptides can be removed from an affinity column using conventional techniques, e.g., by using a high salt elution buffer or by changing pH or other components depending on the affinity matrix utilized. Alternatively, the affinity column comprises an antibody that binds a flt3-L mutant polypeptide. Monoclonal antibodies directed against mutant flt3-L polypeptides may be derived by methods known to those skilled in the art.

Recombinant protein produced in bacterial culture are usually isolated by initial disruption of the host cells, centrifugation, extraction from cell pellets (for insoluble polypeptides), or from the supernatant fluid (for soluble polypeptides), followed by one or more concentration, salting-out, ion exchange, affinity purification or size exclusion chromatography steps. RP-HPLC can be employed for final purification steps. Microbial cells can be disrupted by any convenient method, including freeze-thaw cycling, sonication, mechanical disruption, or use of cell lysing agents.

Transformed yeast host cells can be employed to express flt3-L mutant polypeptides as secreted polypeptides in order to simplify purification. Secreted recombinant polypeptide from a yeast host cell fermentation can be purified by methods analogous to those disclosed by Urdal et al., *J. Chromatog.* 296:171 (1984), which describes two sequential, reversed-phase HPLC steps for purification of a recombinant protein on a preparative HPLC column.

Therapeutic Applications of flt3-L Mutant Polypeptides and Nucleic Acids

Flt3-L induces the proliferation and differentiation of cells expressing the flt3 receptor. Flt3 has been found to be expressed in the brain, placenta, tissues of nervous and hematopoietic origin, testis, ovaries, lymph node, spleen, thymus and fetal liver, as well as in leukemias, including acute myelogenous leukemia (AML) and acute lymphocytic leukemias (T-ALL and B-ALL). Flt3-L induces proliferation of hematopoietic progenitor or stem cells, as well as T cells, early B cells, and erythrocytes. In addition, flt3-L induces the differentiation of hematopoietic progenitor cells into cell types of different lineages, including dendritic cells, facilitating cells, and NK cells. Flt3-L mutant polypeptides can therefore be used to treat a variety of conditions associated with damage to these tissues and cell types.

Since wild type flt3-L has been shown to stimulate T cell proliferation (see U.S. Pat. No. 5,554,512), flt3-L mutant polypeptides can be used to treat patients infected with human immunodeficiency virus (HIV). Such treatment includes in vivo administration of mutant flt3-L polypeptides, to stimulate proliferation in vivo of $CD4^+$ T cells, as well as ex vivo expansion of isolated T cells. Treatment with flt3-L mutant polypeptides would elevate or maintain an HIV-infected patient's immune response. In addition, in vivo treatment would stimulate cells of the erythroid lineage, thereby improving a patient's hematocrit and hemoglobin levels.

Flt3-L mutant polypeptides can be administered either alone or in sequential or concurrent combination with cytokines including interleukins (IL), such as IL-1, IL-2, IL-3, IL-4, IL-5, IL-6, IL-7, IL-8, IL-9, IL-10, IL-11, IL-12, IL-13, IL-14 or IL-15; a colony stimulating factor (CSF) selected from the group consisting of G-CSF, GM-CSF, M-CSF, or GM-CSF/IL-3 fusion proteins; or other growth factors such as Stem Cell Factor (SCF), erythropoietin (EPO), leukemia inhibitory factor (LIF), fibroblast growth factor (FGF) or thrombopoietin (TPO).

The use of flt3-L mutant polypeptides to stimulate production of erythroid cells in vivo for the treatment of anemia is also included in the invention. Such use comprises administering a flt3-L mutant polypeptide to a patient in need of such erythroid cell stimulation, in conjunction with or following cytoreductive therapy. The treatment can include co-administration of another growth factor, including but not limited to those listed above.

The invention also includes the use of flt3-L in peripheral blood progenitor or stem cell transplantation procedures. Typically, peripheral blood progenitor cells or stem cells are removed from a patient prior to myelosuppressive cytoreductive therapy, and then readministered to the patient concurrent with or following cytoreductive therapy, to counteract its myelosuppressive effects. The invention provides for the use of an effective amount of a mutant flt3-L polypeptide in at least one of the following manners: (i) a flt3-L mutant polypeptide is administered to the patient prior to collection of the progenitor or stem cells to increase or mobilize the numbers of such circulating cells; (ii) following collection of the patient's progenitor or stem cells, a mutant flt3-L polypeptide is used to expand such cells ex vivo; and (iii) a mutant flt3-L polypeptide is administered to the patient following transplantation of the collected progenitor or stem cells to facilitate engraftment thereof. The transplantation method of the invention can further comprise the use of an effective amount of a another cytokine, such as those listed above, sequentially or concurrently with a flt3-L mutant polypeptide. Flt3-L mutant polypeptides are useful for autologous, syngeneic and allogeneic cell transplantations.

The invention further includes the use of flt3-L mutant polypeptides to expand progenitor or stem cells collected from umbilical cord blood. The expansion may be performed with a flt3-L mutant polypeptide alone, or sequentially or concurrently with a cytokine from the group listed above.

The term "autologous transplantation" is described in U.S. Pat. No. 5,199,942. Briefly, the term means a method for conducting autologous hematopoietic progenitor or stem cell transplantation, comprising: (1) collecting hematopoietic progenitor cells or stem cells from a patient prior to cytoreductive therapy; (2) expanding the hematopoietic progenitor cells or stem cells ex vivo with flt3-L to provide a cellular preparation comprising increased numbers of hematopoietic progenitor cells or stem cells; and (3) administering the cellular preparation to the patient in conjunction with or following cytoreductive therapy. Progenitor and stem cells may be obtained from peripheral blood harvest or bone marrow explants. Optionally, one or more cytokines, selected from the group listed above, can be combined with a flt3-L mutant polypeptide to aid in the proliferation of particular hematopoietic cell types, or affect the cellular function of the resulting proliferated hematopoietic cell population. Of the above-listed cytokines, SCF, IL-1, IL-3, EPO, TPO, G-CSF, GM-CSF and GM-CSF/IL-3 fusion proteins are preferred, with G-CSF, GM-CSF and GM-CSF/IL-3 fusions being especially preferred. The term "allogeneic transplantation" means a method in which bone marrow or peripheral blood progenitor cells or stem cells are removed from a mammal and administered to a different mammal of the same species. The term "syngeneic transplantation" means bone marrow transplantation between genetically identical mammals.

The transplantation method of the invention described above optionally comprises a preliminary in vivo procedure comprising administering a flt3-L polypeptide alone or in sequential or concurrent combination with a recruitment growth factor to a patient, to recruit hematopoietic cells into peripheral blood prior to harvest. Suitable recruitment factors are listed above, with SCF, IL-1 and IL-3 being preferred.

The method described above optionally comprises a subsequent in vivo procedure comprising administering to a patient a flt3-L mutant polypeptide alone, or in sequential or concurrent combination with an engraftment growth factor to a patient following transplantation of the cellular preparation, to facilitate engraftment and augment proliferation of engrafted hematopoietic progenitor or stem cells from the cellular preparation. Suitable engraftment factors are listed above, with GM-CSF, G-CSF, IL-3, IL-1, TPO, EPO and GM-CSF/IL-3 fusion proteins being preferred.

Flt3-L mutant polypeptides and nucleic acids can also be used to induce the differentiation of certain cells in vivo and in vitro. For example, large quantities of dendritic cells can be generated from $CD34^+$ hematopoietic progenitor cells using the flt3-L mutant polypeptides of the invention. Following collection of $CD34^+$ hematopoietic progenitors and stem cells, flt3-L mutant polypeptides can be used to expand such cells in vitro (also known as ex vivo expansion) and to drive such $CD34^+$ cells to differentiate into dendritic cells of the lymphoid or myeloid lineage. The resulting collection of dendritic cells can be administered to a patient to provide a stronger and improved immune response to an antigen. Alternatively, the resulting dendritic cells can be used as a vaccine adjuvant and can be administered prior to, concurrently with or subsequent to antigen administration. As vaccine adjuvants, flt3-L mutant polypeptides can generate large quantities of dendritic cells and other intermediate cells in vivo to more effectively present antigen. The overall response is a stronger and improved immune response and more effective immunization to the antigen.

A procedure for "ex vivo expansion" of hematopoietic stem and progenitor cells is described in detail in U.S. Pat. No. 5,199,942. Briefly, the method includes the steps of collecting $CD34^+$ hematopoietic stem and progenitor cells from a patient from peripheral blood harvest or bone marrow explants and expanding such cells ex vivo. In addition to the cellular growth factors described in U.S. Pat. No. 5,199,942, other factors such as flt3-L, IL-1, IL-3, or c-kit ligand can be used.

A variety of cell selection techniques are known for identifying and separating $CD34^+$ hematopoietic stem or progenitor cells from a population of cells. Methods and materials for identifying and selecting such cell types are known. Typically, the first step is to collect bone marrow or peripheral blood cells using conventional procedures. Peripheral blood progenitor cells (PBPC) and peripheral blood stem cells (PBSC) can be collected using apheresis procedures known in the art. See, for example, Bishop et al., *Blood*, vol. 83, No. 2, pp. 610–616 (1994). Briefly, PBPC and PBSC are collected using conventional devices, for example, a Haemonetics Model V50 apheresis device (Haemonetics, Braintree, Mass.). Four hour collections are performed typically no more than five times weekly until, for example, approximately $6.5 \times 10^8$ mononuclear cells (MNC)/kg patient are collected. The cells are suspended in standard media and then centrifuged to remove red blood cells and neutrophils. Cells located at the interface between the two phases (i.e., the buffy coat) are withdrawn and resuspended in HBSS. The suspended cells are predominantly mononuclear and a substantial portion of the cell mixture are early stem cells.

Hematopoietic progenitor and stem cells are then isolated from the mononuclear cell fraction by any of a variety of procedures known to those skilled in the art. For example, monoclonal antibodies can be used to bind to a marker protein or surface antigen protein found on stem or progenitor cells. Such markers or cell surface antigens for hematopoietic stem cells include flt3, CD34 and Thy-1. Monoclonal antibodies recognizing these antigens have been described. See, e.g., U.S. Pat. No. 4,714,680 (Anti-My-10). Antibody specific for CD34 is commercially available from Becton Dickinson, Franklin Lakes, N.J., and anti-Thy-1 monoclonal antibodies can be readily generated using the methods described by Dalchau et al., *J. Exp. Med.* 149:576 (1979). A flt3 receptor binding protein also may be used, such as a monoclonal antibody specific for flt3, or the flt3-ligand. The cell binding protein is brought into contact with the collected cell mixture, and the combination is allowed to incubate for a period of time sufficient to permit the binding of the desired cell to the cell binding protein. Undesired cells and cell matter are removed, providing a relatively pure population of stem cells. Stem or progenitor cells having the CD34 marker constitute only about 1% to 3% of the mononuclear cells in the bone marrow. The amount of $CD34^+$ stem or progenitor cells in the peripheral blood is approximately 10- to 100-fold less than in bone marrow.

Isolation of hematopoietic stem or progenitor cells can be performed by using, for example, affinity chromatography, antibody-coated magnetic beads, or antibodies fixed to a solid matrix, such as glass beads, flasks, etc. Antibodies that recognize a stem or progenitor cell surface marker can be fused or conjugated to other chemical moieties including biotin, which can be removed with an avidin or a streptavidin moiety secured to a solid support, or fluorochromes useful in fluorescence activated cell sorting (FACS). Preferably, isolation is accomplished by an immunoaffinity column. Immunoaffinity columns can take any form, but usually comprise a packed bed reactor. The packed bed in these bioreactors is preferably made of a porous material having a substantially uniform coating of a substrate. The porous material, which provides a high surface area-to-volume ratio, allows for the cell mixture to flow over a large contact area while not impeding the flow of cells out of the bed. Typical substrates include avidin and streptavidin, while other conventional substrates can be used. The substrate should, either by its own properties, or by the addition of a chemical moiety, display high-affinity for a moiety found on the cell-binding protein such as a monoclonal antibody. The monoclonal antibodies recognize a cell surface antigen on the cells to be separated, and are typically further modified to present a biotin moiety. It is well known that biotin has a high affinity for avidin, and the affinity of these substances thereby removably secures the monoclonal antibody to the surface of the packed bed. Such columns are well known in the art. See Berenson et al., *J. Cell Biochem.*, 10D:239 (1986).

The column is washed with a PBS solution to remove unbound material, and target cells can be released from the beads using conventional methods. Immunoaffinity columns of the type described above that utilize biotinylated anti-CD34 monoclonal antibodies secured to an avidin-coated packed bed are described for example, in PCT Publ. No. WO 93/08268. A variation of this method utilizes cell binding proteins, such as the monoclonal antibodies or flt3-L as described above, removably secured to a fixed surface in the isolating means. The bound cell binding protein is then contacted with the collected cell mixture and allowed to incubate for a period of time sufficient to permit isolation of the desired cells.

Alternatively, the monoclonal antibodies that recognize the cell surface antigens can be labeled with a fluorescent label, e.g., chromophore or fluorophore, and separated by cell sorting according to the presence of absence or the amount of labeled product.

An alternative means of selecting quiescent stem cells is to induce cell death in the dividing, more lineage-committed, cell types using an antimetabolite such as 5-fluorouracil (5-FU) or an alkylating agent such as 4-hydroxycyclophosphamide (4-HC). The non-quiescent cells are stimulated to proliferate and differentiate by the addition of growth factors that have little or no effect on the stem cells, making the non-quiescent cells more vulnerable to the cytotoxic effects of 5-FU or 4-HC. See Berardi et al., Science 267:104 (1995).

Isolated stem cells can be frozen in a controlled rate freezer (e.g., Cryo-Med, Mt. Clemens, Mich.), and stored in the vapor phase of liquid nitrogen. Ten percent dimethylsulfoxide can be used as a cryoprotectant. After all collections from a donor have been made, the stem cells are thawed and pooled. To induce expansion of the stem cell population in vitro, the cells are incubated in growth medium, such as McCoy's 5A medium, including 0.3% agar, a flt3-L mutant polypeptide, and optionally an additional growth factor, e.g., recombinant human GM-CSF, IL-3, and recombinant human GM-CSF/IL-3 fusion molecules (PIXY321), at concentrations of approximately 200 U/mL, at 37° C. in 5% $CO_2$ in fully humidified air for 14 days. Optionally, human IL-1α or IL-4 may be added to the cultures. A preferred additional growth factor is IL-3 or a GM-CSF/IL-3 fusion protein.

Flt3-L mutant polypeptides can also be used to induce hemapoietic cells to differentiate, e.g., into dendritic cells. To induce differentiation, collected cells, e.g., $CD34^+$ cells, are exposed to either a flt3-L mutant polypeptide alone or in concurrent or sequential combination with one or more of the following cytokines: GM-CSF or another colony stimulating factor (CSF), erthyopoietin (EPO), thrombopoietin (TPO), Tumor Necrosis Factor α (TNF-α), an interleukin, c-kit ligand or a GM-CSF/IL-3 fusion protein. The $CD34^+$ cells are then allowed to differentiate and commit to cells of the dendritic lineage. The resulting dendritic cells are collected and can either be (a) administered to a patient in order to augment the immune system and T-cell mediated or B-cell mediated immune responses to antigen, (b) exposed to an antigen prior to administration of the dendritic cells into a patient, (c) transfected with a gene encoding an antigen-specific polypeptide, or (d) exposed to an antigen and then allowed to process and present the antigen, ex vivo, to T cells collected from the patient followed by administration of the antigen-specific T cells to the patient.

The invention allows the use of an effective amount of flt3-L mutant polypeptide to increase or mobilize dendritic cells in vivo, for example, in a patient's peripheral blood or other tissue or organs, such as the spleen. By increasing the quantity of the patient's dendritic cells, such cells may themselves be used to present specific antigen to T cells. For example, the antigen may be one that already exists within the patient, such as a tumor, bacterial or viral antigen. Flt3-L mutant polypeptides may be used, therefore, to boost the patient's lymphocyte-mediated (e.g., T cell or B cell-mediated) or myeloid-mediated immune response to the already present antigens, resulting in a more effective antigen presentation to the patient's cells. Alternatively, flt3-L mutant polypeptides are administered prior to, concurrently with or subsequent to administration of an antigen to a patient for immunization purposes.

Flt3-L mutant nucleic acids are also used for gene therapy. Gene therapy procedures include those in which cells transfected with exogenous DNA are administered to a host and allowed to engraft. See e.g., Boggs, International J. Cell Cloning, 8:80–96 (1990); Kohn et al., Cancer Invest. 7(2): 179–192 (1989); Lehn, Bone Marrow Transpl. 5:287–293 (1990); Verma, Scientific American pp. 68–84 (1990). One method of transferring a gene to a mammal comprises the steps of culturing early hematopoietic cells in media comprising a flt3-L mutant polypeptide alone or in sequential or concurrent combination with a cytokine selected from the group listed above; transfecting the cultured cells with the exogenous gene; and administering the transfected cells to the mammal.

Pharmaceutical Compositions of Flt3-L Mutants

Pharmaceutical compositions of mutant flt3-L polypeptides are used to treat conditions in which modulation of flt3-L activity is desirable. Such conditions include myelodysplasia, aplastic anemia, HIV infection and AIDS, and cancer.

The pharmaceutical compositions can include growth factors or cytokines in addition to mutant flt3-L peptides or polypeptides. Such growth factors and cytokines include, but are not limited to, interleukins (IL), including IL-1, IL-2, IL-3, IL-4, IL-5, IL-6, IL-7, IL-8, IL-9, IL-10, IL-11, IL-12, IL-13, IL-14 or IL-15; a colony stimulating factor (CSF) selected from the group consisting of G-CSF, GM-CSF, M-CSF, or GM-CSF/IL-3 fusion proteins; or other growth factors such as Stem Cell Factor (SCF), erythropoietin (EPO), thrombopoietin (TPO), leukemia inhibitory factor (LIF) or fibroblast growth factor (FGF). Isolated polypeptides can be further purified by methods known to those skilled in the art, e.g., HPLC. See, e.g., Fisher, Laboratory Techniques in Biochemistry and Molecular Biology Work et al., eds., Elsevier, 1980. Peptides can be synthesized by methods that are known to those skilled in the art. See, e.g., Solid Phase Peptide Synthesis, 2d ed., The Pierce Chemical Company, Rockford, Ill., 1984.

Pharmaceutical compositions also include nucleic acids encoding mutant flt3-L polypeptides. These nucleic acids are administered in a manner allowing their uptake and expression by cells in vivo. Compositions containing nucleic acids are prepared for administration by methods that are routine for those skilled in the art.

Pharmaceutical compositions can include one or more compounds, e.g., nucleic acids, peptides, or polypeptides, and a pharmaceutically acceptable carrier. Pharmaceutically acceptable carriers are biologically compatible vehicles, e.g., physiological saline, which are suitable for administration to a patient.

Nucleic acids can be administered to a patient by standard vector and/or gene delivery systems. Suitable gene delivery systems include liposomes, receptor-mediated delivery systems, naked DNA and viral vectors such as herpes viruses, retroviruses, adenoviruses and adeno-associated viruses.

Flt3-L mutants can be formulated according to known methods used to prepare pharmaceutically useful compositions. Flt3-L mutants can be combined in admixture, either as the sole active material or with other known active materials, with pharmaceutically suitable diluents (e.g., Tris-HCl, acetate, phosphate), preservatives (e.g., Thimerosal, benzyl alcohol, parabens), emulsifiers, solubilizers, adjuvants and/or carriers. Suitable carriers and their formulations are described in Remington's Pharmaceutical Sciences, 16th ed., Mack Publishing Co., 1980. In addition, such compositions can contain mutant flt3-L complexed with polyethylene glycol (PEG), metal ions, or incorporated into polymeric compounds such as polyacetic acid, polyglycolic acid, hydrogels, etc., or incorporated into liposomes, microemulsions, micelles, unilamellar or multilamellar vesicles, erythrocyte ghosts or spheroblasts. Such compositions will influence the physical state, solubility, stability, rate of in vivo release, and rate of in vivo clearance of flt3-L mutants. Flt3-L mutants can also be conjugated to antibodies against tissue-specific receptors, ligands or antigens, or coupled to ligands of tissue-specific receptors. Where flt3 is found on neoplastic cells, flt3-L mutants may be conjugated to a toxin whereby the flt3-L mutant is used to deliver the toxin to the specific site, or may be used to sensitize such neoplastic cells to subsequently administered anti-neoplastic agents.

Flt3-L mutant polypeptides can be administered topically, parenterally, or by inhalation. The term "parenteral" includes subcutaneous injections, intravenous, intramuscular, intracisternal injection, or infusion techniques. These compositions will typically contain a therapeutically effective amount of a flt3-L mutant, alone or in combination with an effective amount of any other active material. Dosages for particular patients depend upon many factors, including intended use, the patient's size, body surface area, age, the particular substance to be administered, time and route of administration, general health and other drugs being administered concurrently. Preliminary doses can be determined according to animal tests, and the scaling of dosages for human administration can be performed according to established methods. A typical dose of polypeptide, peptide or nucleic acid to be administered to a patient is 100 μg per kilogram of body weight.

Mutant Polypeptides of Flt3-L-Related Growth Factors

The identification of the key protein residues involved in flt3-L binding to flt3 allows the production of novel mutants of related growth factor polypeptides that can bind to and activate flt3-expressing cells. Such growth factors include Macrophage Stimulating Factor (M-CSF), and Stem Cell Factor (SCF). These proteins, which have a high degree of structural similarity to flt3-L, can be mutagenized at residues corresponding to those involved in flt3-L binding to flt3. For example, SCF (also known as c-kit ligand, Steel Factor (SF) and Mast Cell Growth Factor), is a hematopoietic growth factor that binds the c-kit receptor. See WO 97/38101. Therapeutic use of SCF is hampered by its ability to stimulate mast cells. Mast cell stimulation can result in toxic effects in vivo, including histamine release and respiratory distress. See Lyman, *Intl. J. Hematol*. 62:63–73 (1995). Mutant SCF polypeptides of the invention maintain activity as hematopoietic growth factors, but do not stimulate mast cells. The invention also includes small molecules which incorporate key residues for flt3 binding, and which maintain a three dimensional structure that allows binding to and activation of flt3-expressing cells.

EXAMPLES

Example 1

Generation of and Screening for flt3-L Mutants

The screening assay in which flt3-L mutants were identified utilized a flt3-L expression vector, which was subjected to random mutagenesis. Yeast were transformed using the mutagenized vectors, and subjected to a filter binding assay to detect secreted proteins. Proteins corresponding to flt3-L mutants were detected by reaction with an anti-flt3-L antibody, followed by a flt3-Fc fusion protein, and HRP-goat anti-human IgG, Fcγ conjugate, as described below.

Construction of a Flt3-L Expression Vector

The flt3-L expression vector was constructed by inserting human flt3-L nucleic acid into the multicopy expression vector, paADH2. The sequence of a wild type flt3-L cDNA is disclosed in U.S. Pat. No. 5,554,512, and is set forth herein as SEQ ID NO:2. The paADH2 plasmid contains the 2μ origin of replication and the ADH2 promoter to drive expression of foreign genes, and the α-factor to direct secretion of heterologous proteins. Price et al., *Gene* 55:287–293 (1987). The PIXY456 expression vector is derived from paADH2 by addition of a BamH1 site adjacent to the ASP718 site. Primers JM37 (5'-ATTAGGTACCTTTGGATAAAAGACTCAGTGGGACCAGGAC-3') (SEQ ID NO: 3) and P11673 (5'-ATATGGATCCCTACGGGGCTGTGGCCTCCAGGGGCCG-3') (SEQ ID NO: 4) were used to amplify human flt3-L from flt3-L clone 9 cDNA (Lyman et al., *Blood* 83:2795–2801 (1994)). JM37 primer contains an ASP718 site 20 bases from the 3' end of the α-factor, and fuses the α-factor leader to the flt3-L PCR product. P11673 contains a BamH1 site for cloning into PIXY456. The amplified flt3-L fragment was digested with Asp718 and BamH1 and ligated into PIXY456 to construct PIXY771. The NFS glycosylation site at positions 123–125 of the flt3-L gene was mutated to NFA using primer JM40 (5'-CCTCCTGCAGGAGACCTCCGAGCAGCTGGTGGCGCTGAAGCCCTGGATCACTCGCCAGAACTTCGCCCGGTGCCTGG-3') (SEQ ID NO: 5). Primers JM40 and P11673 were used to amplify the 3' end of the human flt3-L gene. This amplified fragment was digested with BsaI and BamH1 and used to replace the BasI-BamH1 fragment in PIXY771, resulting in plasmid PIXY797. All constructs were confirmed by DNA sequence analysis.

Mutagenesis and Transformation

The flt3-L expression vector was subjected to random mutagenesis and used to transform yeast. Mutagenic PCR was performed as previously described (Leung et al., *Technique* 1:11–15 (1989)). DNA sequence analysis identified 100 point mutations, including silent mutations, from 59 clones. The flt3-L nucleotide lesions obtained included transitions (49 A/T→G/C, 18 G/C→A/T) and transversions (21 A/T→T/A, 3A/T→C/G, 7 G/C→T/A, 2 G/C→C/G).

Yeast transformations were performed by homologous recombination (Muhlard et al., *Yeast* 8:79–82 (1992)). In these transformations, gel-purified gapped vector DNA and the flt3-L PCR fragment were added to LiOAc-treated yeast. The flt3-L PCR product contains 30 bp 5' to and 60 bp 3' to the wild type flt3-L gene. These two regions are homologous to the regions immediately adjacent to the gap in the vector DNA. Transformed yeast were plated on YNB (-trp) selective medium (Sherman, *Methods Enzymol*. 194:3–21 (1991)) and grown at 30° C. until individual colonies were 0.5 to 2 mm in diameter, about 2 to 3 days.

Screening Assay to Detect Flt3-L Mutants

The transformed yeast colonies were then used in the screening assay, as described below. Colonies of 0.5 to 2 mm in diameter were lifted onto cellulose acetate membranes. A second "capture" membrane, made of nitrocellulose, was coated with 0.1 mg/ml M5α-flt3-L, a monoclonal antibody that specifically binds flt3-L, in 50 mM phosphate, pH 7.4, 150 mM NaCl (PBS) for 16 hours at 4° C. M5α-flt3-L is a non-neutralizing antibody that binds flt3-L without interfering with the flt3-flt3-L binding interaction. Progressive deletions of flt3-L indicate that residues carboxy-terminal to cys-131 are dispensable for normal activity, but are required for binding to M5α-flt3-L. Lyman et al., *Blood* 86:4091–4096 (1995).

The capture membrane was subsequently blocked for four hours at 4° C. in blocking solution (PBS containing 3% (w/v) BSA, 5% (w/v) nonfat dry milk), then washed twice in PBS. The wet capture membrane was then placed on a YEPD plate (Sherman, *Methods Enzymol*. 194:3–21 (1991)), taking care to avoid air pockets. The capture membrane was then covered with the cellulose acetate membrane with the yeast colonies uppermost, again taking care to avoid air pockets. The membrane sandwich was marked by needle puncture for orientation, and the assembly was incubated at 30° C. for 18 to 22 hours. The cellulose acetate membrane with colonies was removed and placed on a fresh YEPD plate (Sherman, *Methods Enzymol.* 194:3–21 (1991)) and stored at 4° C. for later recovery of the yeast.

The capture membrane was then used to detect flt3 binding to the immobilized flt3-L mutant proteins. This protocol was carried out at room temperature and all reagents and washes were in PBS containing 1% (w/v) BSA, unless otherwise stipulated. The capture membrane was blocked for one hour in blocking solution. After washing three times, the membrane was probed for one hour with 0.5 µg/ml human flt3-Fc. This soluble form of the human flt3 protein was constructed using a protocol previously used to make a soluble form of the murine flt3 protein (described in Lyman et al., *Cell* 75:1157–1167 (1993)). Human flt3 nucleic acid was amplified by PCR and cloned, as previously described (Rosnet et al., *Blood* 82:1110–1119 (1993)). In the flt3-Fc polypeptide, the entire extracellular domain of the human flt3 (ending at the amino acid just before the start of the transmembrane region) is fused to the Fc portion of human immunoglobulin G (IgG). Flt3-Fc fusion protein expressed in 293/EBNA cells was purified using protein A-Sepharose (Pharmacia).

After being probed with flt3-Fc, the membrane was washed three times over 10 minutes, then probed for one hour with 0.53 µg/ml HRP-goat anti-human IgG, Fcγ conjugate (Jackson Immuno Research Laboratories). The membrane was then washed three times over 30 minutes in PBS, and developed with 4-chloro-1-naphthol (BioRad) in PBS plus 18% methanol and 0.002% hydrogen peroxide. The enzymatic reaction was typically stopped after 10 to 15 minutes by washing in distilled water, followed by drying.

Single yeast colonies whose receptor binding signal differed from the wild type background were isolated and plated on selective medium. Colonies were identified and isolated by alignment of the two membranes via previously made needle puncture marks. Two ml YEPD cultures of the chosen colonies were grown for three days at 30° C., after which the cells and supernatant were separated by centrifugation (12,000 rpm, Beckman microfuge, 5 minutes, 22° C.). Cells were stored at −20° C. for later retrieval of plasmid DNA for sequencing and subcloning. Supernatants were used immediately for subsequent screens, or stored at 4° C.

Example 2

Characterization of Flt3-L Mutant Polypeptides

Identification of Flt3-L Mutant Polypeptides

The receptor-binding properties of the secreted flt3-L mutants were assessed visually by noting the variation from wild type flt3-L in intensity of the stained spots after the enzyme-linked reaction. Most colonies secreted flt3-L which stained similarly to wild type. About 1% of the colonies, however, gave rise to colonies devoid of stain. These clear white colonies were designated as receptor-binding deficient (flt3-L-), and were isolated by reference to their positions on the cellulose acetate membrane. The appearance of stained spots whose intensity was greater than that of wild type was a far more rare event. These dark colonies were isolated and designated flt3-L$^{++}$, to indicate increased receptor binding properties over wild type. Approximately 60,000 colonies were screened, with up to 300 colonies assayed per standard size petri dish (82 mm diameter). All of the detectable flt3-L$^{++}$ colonies (114 total) were isolated, along with 214 flt3-L$^-$ colonies, which represented only a portion of the flt3-L$^-$ species.

Electrophoresis and Western Blotting

Supernatants from all of the flt3-L$^-$ and flt3-L$^{++}$ yeast cultures were analyzed by Western blot, to assess the amount and quality of mutant flt3-L protein being secreted by individual yeast colonies. The buffers, stains, polyacrylamide gels and PVDF membrane used for electrophoresis were purchased from Novex, and electrophoresis was performed as described by the manufacturer. For Western blot analysis, yeast supernatants were run on 4–20% SDS-polyacrylamide gels and then transferred to PVDF membranes. The blots were probed with the M5α-flt3-L monoclonal antibody (Lyman et al., *Blood* 86:4091–4096 (1995)), followed by HRP-goat anti-rat IgG conjugate (Zymed) and visualized with 4-chloro-1-naphthol reagent (BioRad), according to manufacturer's instructions.

Mutants with low levels of expression or grossly altered structures were eliminated from further study. Of the 214 flt3-L$^-$ colonies, 94 were discarded because little or no protein was secreted, five were discarded because only high molecular weight smears were observed on Western blot, possibly due to hyperglycosylation, and an additional four were discarded due to lower than expected molecular weight. The specific activity of the remaining flt3-L mutant proteins was determined by subjecting supernatant from the yeast colonies secreting the mutant proteins to ELISA and WWF7 cell proliferation assays. These assays to measure the level of expression of a particular flt3-L mutant polypeptide, and its biological activity, respectively. The ELISA assay has been previously described (Lyman et al., *Oncogene* 10:147–149 (1995)). Biological activity, as tested in the murine WWF7 cell assay, was assessed using [$^3$H] thymidine incorporation assays, according to previously published protocols (Brasel et al., *Leukemia* 9:1212–1218 (1995)). Species with low levels of protein expression or specific activities near that of wild type were discarded. The remaining 30 flt3-L$^-$ species were subjected to DNA sequence analysis. A similar process was used to select 29 flt3-L$^{++}$ species for DNA sequence analysis.

For sequence analysis, plasmid DNA was rescued from yeast clones and sequenced with synthetic primers that hybridize to the coding and noncoding strands of the vector DNA 5' and 3' the flt3-L gene. The results are shown in Table 1. The flt3-L mutant polypeptides are designated by a first letter, followed by a number, followed by a second letter. The first letter is the one-letter abbreviation for an amino acid found in the mature human flt3-L polypeptide. The number in the designation is the position of that amino acid in mature human wild type human flt3-L (SEQ ID NO:18). The second letter in the designation is the one-letter abbreviation for the amino acid found at that position in the mutant flt3-L polypeptide. For example, D3G refers to a mutant in which Glycine (G) has been substituted for the Aspartic Acid (D) at position 3 of the mature wild type flt3-L protein (SEQ ID NO:18).

Since amino acids 1–26 of the full length flt3-L protein (SEQ ID NO:1) are cleaved to produce the mature protein, the first amino acid of the mature wild type human flt3-L polypeptide (SEQ ID NO:18) is the threonine at position 27 of the full length polypeptide (SEQ ID NO:1). A negative number in a designation, e.g., −3 in L-3H, refers to the -3 position of the mature human flt3-L wild type polypeptide, i.e., position 24 of the full length flt3-L polypeptide (SEQ ID NO:1). In the sequence listing, for mutations occurring within the mature flt3-L polypeptide, the sequences begin at the threonine at position 27 of the full length protein (SEQ ID NO:1). For mutations occurring outside the mature protein, e.g., L-3H, the position of the mutation is listed as position 1 in the sequence listing. For example, in L-3H, position 1 in the sequence listing corresponds to position 24 in the full length human flt3-L polypeptide (SEQ ID NO:1).

Table 1 is divided into two sections, one showing species that were designated as deficient in receptor binding (flt3-L⁻), and the other showing species that were designated having increased receptor binding (flt3-L⁺⁺), according to the results of the initial filter binding assay. Multiple amino acid substitutions occurred in 13 of the 59 flt3-L DNA sequences. Flt3-L⁻ clones with multiple amino acid substitutions included: L-3F/R95C; T1A/R55L/F96V; D3G/F15Y; D3G/I11F/V113E; P10S/M57V/T62S; I11Y/A35P/F87L; I11Y/L139Q; S13P/M68V; S36P/N37D/L148Q; L96F/S136T. In a number of cases, single mutations were subcloned from flt3-L mutants that had sustained multiple mutations. Subcloning was carried out by inserting various flt3-L mutants into the E. coli vector, pocus-1 (Novagen). The desired flt3-L mutant, having a single mutation, was generated by DNA restriction, fragment isolation, and ligation into appropriate vectors. This procedure allowed the assignment of function to individual residues for some of the multiply-substituted proteins.

TABLE I

Characteristics of Flt3-L Mutants: Yeast Medium

| Mutant[a] | FL:M/SCF:H-M/M-CSF:H-Mb | ELISA[c] (μg/ml) | Sp.Ac.MUT[d] / Sp.Ac. WT | (n)[e] | Independent[f] Isolate, n |
|---|---|---|---|---|---|
| Wild Type Flt3-L − |  | 5.79 | 1.00[g]− | (11) | NA |
| D3G | D/NA/S-S | 3.98 | 0.81 ± 0.09 | (2) | 1[h] |
| H8R | H/R-G/H-H | 5.01 | 0.00 | (3) | 1 |
| S9G | S/N-N/M-M | 2.69 | 0.13 ± 0.06 | (3) | 1 |
| P10S | P/R-P/I-I | 1.83 | 0.00 | (3) | 1[h] |
| I11Y | I/V-V/G-G | 3.06 | 0.00 | (3) | 1[h] |
| S13P | S/N-D/G-G | 5.71 | 0.00 | (4) | 2 |
| S13F | S/N-D/G-G | 1.83 | 0.00 | (2) | 1 |
| F15L | F/V-V/L-L | 3.49 | 0.00 | (2) | 1 |
| F15Y | F/V-V/L-L | 2.26 | 0.19 ± 0.04 | (3) | 1[h] |
| R20C | R/K-K/R-Q | 2.02 | 0.11 ± 0.09 | (2) | 1 |
| R55C | R/D-L/D-D | 2.51 | 0.05 ± 0.03 | (3) | 3 |
| R55L | R/D-L/D-D | 1.58 | 0.29 ± 0.02 | (2) | 1[h] |
| A64T | A/F-F/R-K | 2.46 | 0.09 ± 0.06 | (2) | 1 |
| V75A | V/L-L/L-L | 2.65 | 0.18 ± 0.07 | (2) | 1 |
| F81L | F/D-D/R-N | 1.90 | 0.06 ± 0.03 | (2) | 2 |
| F81S | F/D-D/R-N | 2.71 | 0.00 | (3) | 1 |
| F87L | L/K-E/T-T | 1.22 | 0.01 ± 0.02 | (2) | 1 |
| P90S | L/S-A/Y-Y | 1.92 | 0.09 ± 0.06 | (2) | 1 |
| R95C | R/E-E/R-R | 1.40 | 0.26 ± 0.01 | (2) | 1[h] |
| V113E | L/D-D/N-N | 5.13 | 0.80 ± 0.11 | (2) | 1[h] |
| K116E | K/K-K/K-K | 6.54 | 0.02 ± 0.01 | (2) | 1 |
| F124L | F/T-T/S-T | 2.22 | 0.22 ± 0.06 | (5) | 2 |
| F124S | F/T-T/S-T | 2.22 | 0.00 | (4) | 1 |
| Flt3-L++ |  |  |  |  |  |
| L-3H | N/A | 6.40 | 1.86 ± 0.32 | (3) | 2 |
| H8Y | H/R-G/H-H | 6.07 | 1.71 ± 1.04 | (3) | 1 |
| L26F | L/P-P/M-M | 6.59 | 0.69 ± 0.17 | (3) | 1 |
| L27P | L/.-./E-E | 13.91 | 0.07 ± 0.03 | (4) | 2 |
| V34L | V/L-L/F-F | 3.79 | 0.58 ± 0.15 | (3) | 1 |
| K84E | S/E-L/S-S | 7.34 | 2.88 ± 0.62 | (21) | 14 |
| K84T | S/E-L/S-S | 4.82 | 1.63 ± 0.29 | (2) | 1 |
| W118R | C/F-F/L-L | 4.49 | 2.19 ± 0.19 | (2) | 1 |
| Q122R | Q/S-S/I-I | 4.39 | 2.16 ± 0.25 | (5) | 1 |

[a]Mutants are named using a first letter, followed by a number, followed by a second letter. The first letter is the one-letter abbreviation for a wild type amino acid; the number is the position of that amino acid in wild type mature flt3-L (i.e., flt3-L from which amino acids 1-26 of SEQ ID NO:1 have been removed); and the second letter is the one-letter abbreviation for the replacement amino acid. The first 23 species (i.e., D3G to F124S), are designated as flt3 binding deficient (flt3-L⁻), while the last 9 species (i.e., L-3H to Q122R) are designated as having increased flt3 binding (flt3-L⁺⁺), according to the results of the initial filter binding assay.
[b]The column labeled FL:M/CSF:H-M/M-CSF:H-M refers to the corresponding murine flt3-L (FL:M), human and murine SCF (SCF:H-M) and human and murine M-CSF (M-CSF:H-M) amino acid residues, based on the sequence alignment of native human and murine flt3-L, SCF and M-CSF proteins (Hannum et al., Nature 368:643–648 (1994)).
[c]The level of flt3-L expression as determined by ELISA of yeast supernatants.
[d]Direct assay of yeast supernatants yielded the ratio of cell proliferation activity in WWF7 cells (units/ml) to concentration of flt3-L protein as determined by ELISA (ng/ml). The ratio of specific activity of mutant to wild type flt3-L in a given assay is averaged over one or more independent assays. A value of zero indicates the proliferation activity of the mutant flt3-L protein was below the limit of detection of the assay.
[e]The number of independent assays is represented by n.
[f]Independent isolate, n, refers to the number of times a particular mutation was isolated. NA stands for "not applicable".
[g]The specific activity of WT protein averaged over 11 independent assays equals 0.95 ± 0.34 units/ng.
[h]These mutants were subcloned from species that had multiple amino acid substitutions.

[a]Mutants are named using a first letter, followed by a number, followed by a second letter. The first letter is the one-letter abbreviation for a wild type amino acid; the number is the position of that amino acid in wild type mature flt3-L (i.e., flt3-L from which amino acids 1-26 of SEQ ID NO:1 have been removed); and the second letter is the one-letter abbreviation for the replacement amino acid. The first 23 species (i.e., D3G to F124S), are designated as flt3 binding deficient (flt3-L⁻), while the last 9 species (i.e., L-3H to Q122R) are designated as having increased flt3 binding (flt3-L⁺⁺), according to the results of the initial filter binding assay.

[b]The column labeled FL:M/CSF:H-M/M-CSF:H-M refers to the corresponding murine flt3-L (FL:M), human and murine SCF (SCF:H-M) and human and murine M-CSF (M-CSF:H-M) amino acid residues, based on the sequence alignment of native human and murine flt3-L, SCF and M-CSF proteins (Hannum et al., Nature 368:643–648 (1994)).

[c]The level of flt3-L expression as determined by ELISA of yeast supernatants.

[d]Direct assay of yeast supernatants yielded the ratio of cell proliferation activity in WWF7 cells (units/ml) to concentration of flt3-L protein as determined by ELISA (ng/ml). The ratio of specific activity of mutant to wild type flt3-L in a given assay is averaged over one or more independent assays. A value of zero indicates the proliferation activity of the mutant flt3-L protein was below the limit of detection of the assay.

[e]The number of independent assays is represented by n.

[f]Independent isolate, n, refers to the number of times a particular mutation was isolated. NA stands for "not applicable".

gThe specific activity of WT protein averaged over 11 independent assays equals 0.95±0.34 units/ng.
hThese mutants were subcloned from species that had multiple amino acid substitutions.

The flt3-L mutants isolated and sequenced are shown in Table 1, along with their levels of expression, as determined by ELISA, and specific activities, as determined by the ratio of cell proliferation activity in WWF cells (units/ml) to concentration of flt3-L protein as determined by ELISA. As shown in Table 1, thirty two different amino acid substitutions that alter flt3-L biological activity were found at 24 sites. FIG. 2 is a linear representation of flt3-L amino acid substitutions in the mutants identified in this study. The top of the figure shows the secondary structure of the wild type human flt3-L protein, including the intramolecular disulfide linkage, placement of β-sheet segments, and placement of α-helices A through D based on sequence alignment with the M-CSF protein (Hannum et al. *Nature* 368:643–648 (1994)). The bottom of the figure shows the primary structure of wild type flt3-L, superimposed with the relative specific activity profile of mutants with single amino acid substitutions. Positions at which more than one substituting amino acid were found are represented by the substitution that induced the greatest perturbation in relative specific activity.

As shown in FIG. 2 at bottom, when the collection of 24 positions along the primary structure of flt3-L is plotted, three linear clusters of high frequency amino acid substitution, or mutational "hot spots," appear at positions 8–15, 81–87 and 116–124 of the mature wild type flt3-L polypeptide. Each of the three "hot spots" contains, at positions 8, 84, 118 and 122 of the mature wild type protein, respectively, amino acid substitutions that improve the biological activity of flt3-L. Mapping of these hot spots onto a structural model of flt3-L indicates that mutations on the solvent-exposed surface of the N terminus of helix A, or disruption of the packing of helix A, is deleterious to the function of flt3-L, as indicated by the large number of mutations isolated between positions 8 through 15 of the mature flt3-L protein.

As indicated in Table 1, while some of the flt3 mutant polypeptides contain substitutions at the same position, these substitutions may be by a different amino acid in different mutant polypeptides. For example, in F15Y, phenylalanine is replaced at the 15 position of the mature wild type flt3-L polypeptide by tyrosine, while in F15L, phenylalanine is replaced at this position by leucine. The addition of the single hydroxyl group from the tyrosine side chain in F15Y reduces its activity by 80%, as measured in the WWF7 assay, while the conservative substitution in F15L completely abolishes detectable activity in this assay. The K84E (SEQ ID NO:14) substitution was detected in 14 flt3-L$^{++}$ independent isolates, and one flt3-L$^{++}$ K84T (SEQ ID NO:15) substitution mutant was obtained. In two cases, mutants with a flt3-L$^{++}$ phenotype had an amino acid substitution at the −3 position of mature flt3-L, i.e., a position outside the mature protein. The flt3-L used contains an additional three residues, derived from the signal sequence, which are amino terminal to the threonine that is the first residue of the mature flt3-L protein (SEQ ID NO:18). Amino terminal sequence analysis of wild type protein has confirmed this conclusion. Thus, a substitution outside the mature protein, i.e., the substitution of leucine by histidine at the −3 position, is able to increase flt3-L biological activity. The screen also produced three mutants, R20C, R55C and R95C, that have substitutions introducing cysteine residues.

The L27P mutation (SEQ ID NO:13) occurs at the putative carboxy terminus of helix A of wild type flt3-L, i.e., at the proposed dimerization interface in the model for flt3-L quaternary structure. L27P was isolated in the primary membrane screen as a flt3-L$^{++}$ species, but on secondary screening it was flt3-L$^-$. While L27P was isolated independently twice as a flt3-L$^{++}$ species, its activity is only 7–20% of wild type (see FIG. 1 and Table 1). Since L27P is expressed at almost three times the level of wild type protein, this high level of expression likely accounts for the flt3-L$^{++}$ signal observed in the primary membrane screen. Other mutations identified in the screen that map to the dimerization interface are L26F (SEQ ID NO:12) and A64T (SEQ ID NO:9).

Example 3

Purification and Analysis of Flt3-L Mutant Polypeptides

Flt3-L mutants exhibiting greater than wild type specific activity in the WWF7 assay, as shown in Table 1 (e.g., H8Y (SEQ ID NO:11), K84E (SEQ ID NO:14), K84T (SEQ ID NO:15), W118R (SEQ ID NO:16), and Q122R (SEQ ID NO:17) ), were purified. Mutants with specific activities lower than wild type (e.g., H8R, I11Y, F81S, K116E) were selected for further study based on the relative proximity of their substitutions to mutations resulting in a flt3-L$^{++}$ phenotype, and near wild type levels of expression. The L27P (SEQ ID NO:13) mutant, which is predicted to disrupt the dimerization interface of flt3-L, was also purified.

Preparation of Recombinant Human Flt3-L

Wild type and mutant flt3-L proteins were purified to greater than 90% homogeneity, according to the following protocol. Yeast medium (1.2 L) was filtered through a 0.22 μm membrane. The pH of the medium was adjusted to 4.0 by the addition of glacial acetic acid with rapid mixing, and filtered through a 0.22 μm membrane a second time (conductivity 2–6 mOhms). The filtrate was applied to a 30 ml Fractogel EMD SO3–650 (M) (EM Separations), equilibrated with 25 mM NaCH$_3$COO/50 mM NaCl, pH 4.0 at 20 ml/min. Protein was eluted with 25 nM MES/200 mM NaCl, pH 6.0. The pH was adjusted to 7.5–8 by the addition of ¹⁄₂₀th volume of 1 M Tris, pH 9.0, and the solution was then filtered through a YM100 membrane (Amicon).

Flt3-L was affinity purified by passing the filtrate over a column of the monoclonal antibody M5α-flt3-L conjugated to CNBr-activated Sepharose 4B (Pharmacia), equilibrated in 50 mM NaHPO$_4$/300 mM NaCl, pH 7.4. Protein was eluted with 25 mM NaHPO$_4$, pH 11.3, and the eluant was neutralized by addition of ¹⁄₁₀₀th volume 1 M monobasic phosphate. The eluant was concentrated and applied to a Superdex 200 column (Pharmacia) equilibrated in PBS at 2.5 ml/min. The dimer peak was collected, concentrated, filtered through a 0.22 μm membrane and stored at 4° C. The concentration of purified flt3-L protein was determined by duplicate quantitative amino acid analysis after acid hydrolysis, and the results averaged. The level of contamination of purified protein was assessed visually by running 2–4 μg of various flt3-L proteins on 16% SDS-polyacrylamide gels and stained with colloidal Coomassie stain. In all cases, the proteins were detected as a single species (>90%) with a Mr of 18,000.

The amino acid sequence of the flt3-L protein used to name the mutants identified herein is numbered according to the mature fully processed soluble protein, having the amino terminal residues Thr-Gln-Asp at positions 1–2–3, respectively (i.e., positions 27, 28 and 29 of full length wild type flt3-L (SEQ ID NO:1)), (see Lyman et al, 1994). The gene construct utilized for expression in yeast encodes an additional three amino acids (Leu-Ser-Gly) amino terminal to the mature protein. Amino terminal sequence analysis of purified yeast-derived flt3-L protein shows that 80% of the amino terminal sequence is Leu:Ser:Gly:Thr:Gln:Asp, while 20% begins at the penultimate residue, Serine. The specific activity and $K_{di}$ for receptor binding of this yeast-derived protein ($K_{di}$=0.09 nM) used in this study is similar to flt3-L having native mature sequence ($K_{di}$=0.08 nM), and expressed in mammalian cells, where $K_{di}$ is defined as the dissociation constant of unlabelled flt3-L for flt3, as determined by inhibition of binding of $^{125}$I labelled flt3-L. Therefore, this yeast-derived protein is referred to as wild type flt3-L.

Radiolabeling, Binding Assays, and Data Analysis

Purified recombinant flt3-L was labeled with $^{125}$I using a solid phase chloramine T analog (Iodogen, Pierce Chemical, Rockford, Ill.) to a specific radioactivity of $4 \times 10^{14}$ cpm/mmol with no detectable loss of specific binding activity as assessed by inhibition assays with unlabeled flt3-L.

Figure 3:
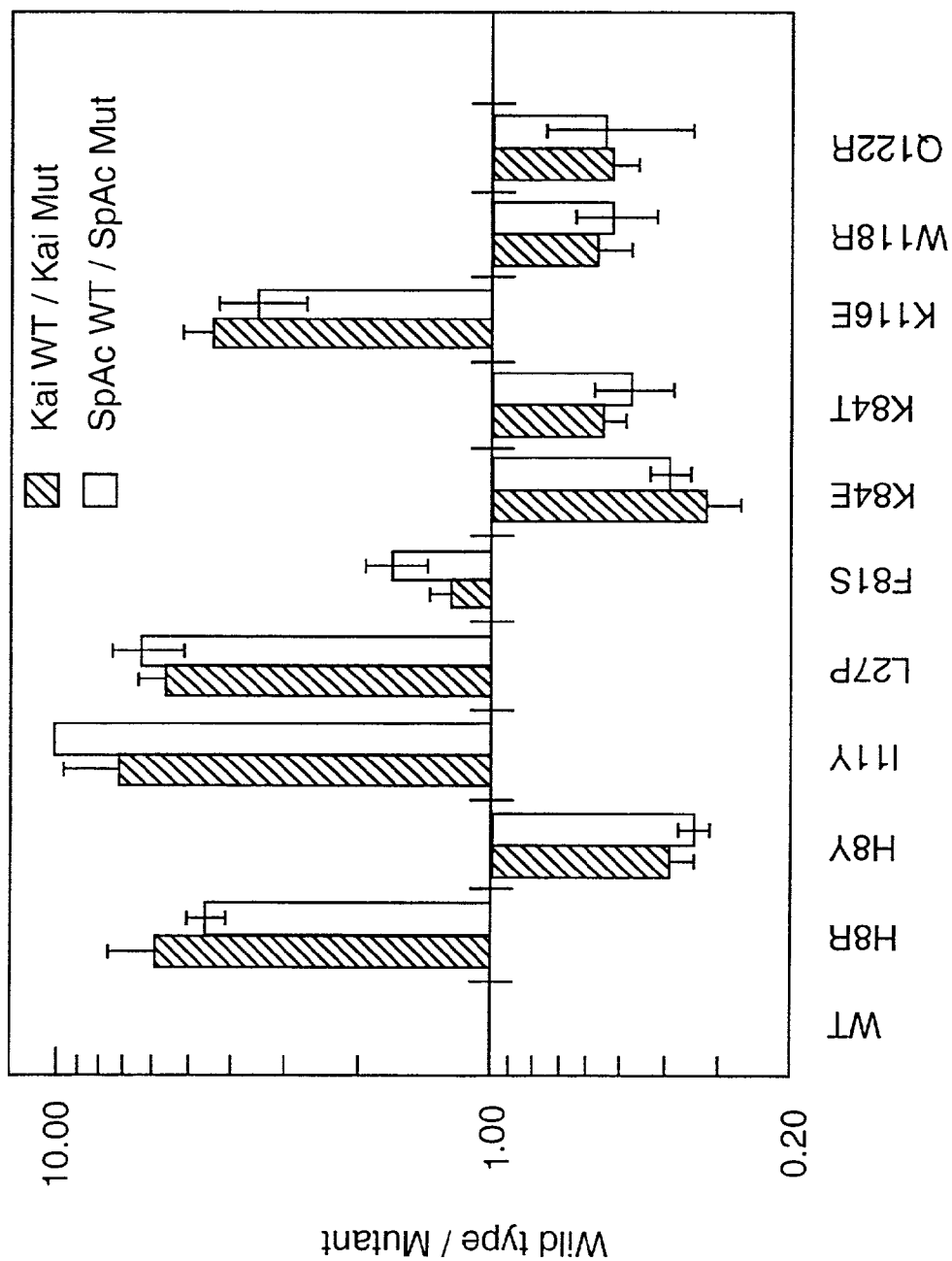
FIG. 3 shows the results of flt3 Receptor (flt3) binding and BAF/hflt3 cell proliferation assays of flt3-L mutant polypeptides relative to wild type flt3-L polypeptide.

Binding assays were performed using a phthalate oil separation method as described previously for murine $^{125}$I-GM-CSF (Park et al., J. Biol. Chem. 261:4177–4183 (1986)). Briefly, BAF-BO3 cells transfected with human flt3 cDNA (0.5–1×10$^6$) were incubated with serial dilutions of $^{125}$I-flt3-L in binding medium (RPMI 1640, 2.5% bovine serum albumin, 0.2% NaN3, 20 mM Hepes, pH 7.2) in 96 well microtiter plates maintained on a mini-orbital shaker (Bellco) at 37° C. for 90 minutes. Inhibition binding assays were carried out by holding the radiolabeled flt3-L concentration constant at 0.3 nM, while the concentration of unlabeled competitor proteins ranged from 150 nM to 0.001 nM. The ratio of $K_{di}$ of mutant to wild type flt3-L, determined in at least duplicate, in a given assay was averaged over at least three independent assays and the standard error of the mean (SEM) reported. The data are shown in FIG. 3. These data were generated using the BAF/hflt3 cell proliferation assay. For this assay, cells expressing human flt3 (BAF/hflt3 cells) were constructed from BAF/B03 cells, using a procedure previously described for producing BAF/B03 cells expressing the murine flt3 (Lyman et al., Cell 75:1157–1167 (1993)). Expression of human flt3 by BAF/hflt3 cells was confirmed by examining the capacity of the cells to proliferate in response to soluble flt3-L, and by flow cytometric analysis using biotinylated flt3-L.

The values of flt3 binding and BAF/hflt3 cell proliferative activity by purified flt3-L mutants are shown in FIG. 3. The ordinate is the $Log^{10}$ of the value relative to wild type flt3-L, and the abscissa is the flt3-L mutant designation. Shown are $K_{ai}$ mutant/$K_{ai}$ wild type (filled bars) and specific activity mutant/specific activity of wild type (open bars). The $K_d$ and $K_{di}$ for wild type protein is 0.13±0.04 nM (SD) and 0.09±0.02 nM (SEM), respectively (n=7). The ratio of $K_{ai}$ mutant to wild type flt3-L, determined in at least duplicate, in a given assay is averaged over at least three independent assays and the standard error of the mean (SEM) is reported.

Specific activity of purified mutant or wild type protein was calculated as the ratio of proliferation activity in BAF/hflt3 cells (units/ml) to concentration of flt3-L protein as determined by amino acid composition (ng/ml). The ratio of specific activity of mutant to wild type flt3-L, determined in duplicate, in a given assay was averaged over at least three independent assays and the standard error of the mean (SEM) is reported. ND stands for "not determined." Using radiolabeled yeast-derived protein, a $k_{di}$ of 0.08±0.01 nM for recombinant CHO-derived human flt3-L, which has native human sequence, was obtained.

Mutations that increase biological activity relative to wild type, i.e., H8Y (SEQ ID NO:11), K84E (SEQ ID NO:14), K84T (SEQ ID NO:15), W118R (SEQ ID NO:16) and Q122R (SEQ ID NO:17), were identified in each of the three flt3-L mutational "hot spots" identified in this study. Two mutations were isolated in which histidine at position 8 in the mature flt3-L polypeptide was substituted, i.e., H8R, which is flt3-L_, and H8Y, which is flt3-L$^{++}$. This histidine is conserved in murine flt3-L and the related cytokine, M-CSF. When the flt3-L and M-CSF protein sequences are aligned, his-8 of the mature flt3-L polypeptide is equivalent to his-9 of M-CSF.

Example 4

Physical Characterization of flt3-L Mutants

The results of physical characterization tests indicate that the isolated flt3-L mutant polypeptides maintain the structure of the native flt3-L polypeptide. As detailed below, flt3-L mutants were found to maintain the dimeric structure and the helical content of wild type flt3-L.

Determination of Stokes Radius in Purified Flt3-L Mutants

Stokes radius was measured in purified flt3-L mutants in the following manner. Gel filtration chromatography of purified proteins was performed on a 300×7.8 mm Bio-Sil 125–5 column (RioRad) in PBS at a flow rate of 1 ml/min. The elution profiles were monitored at an absorbance wavelength of 280 nm. The proteins were loaded on the column at 45 μg injections at a concentration of 0.1 mg/ml. Standard globular proteins were loaded at a concentration of 0.1 mg/ml and included thyroglobulin, gamma globulin, bovine serum albumin, ovalbumin, carbonic anhydrase, myoglobin, and cytochrome C (MW=670, 158, 66, 44, 29, 17, 12.4 kDa, respectively). A calibration curve was constructed by plotting log M vs $K_{sec}$, where $K_{sec}$=(Ve−Vo)/(Vt−Vo), where Vo is the void volume as determined by thyroglobulin; Vt, the total volume as determined by NaN$_3$; and Ve, the elution volume of the target protein. The Stokes radius of purified flt3-L was determined in duplicate and the mean value is reported in Table 2.

Circular Dichroism Analysis of Flt3-L Mutant Polypeptides

Circular dichromism spectra of proteins were obtained using a Jasco 500 c spectropolarimeter interfaced with an IBM AT computer. Raw data (ellipticities) were processed, after averaging and correction for appropriate solvent blanks, according to the equation: MRE=[θ$_{obs}$] (MRW)]/101c, where MRE is the mean residue ellipticity in (deg) (cm$^2$)/dmol, θ$_{obs}$ is the observed ellipticity in mdeg, and MRW is the mean residue weight, 1 is the cell pathlength in cm, and c is the concentration of protein g/ml. All spectra were measured in a 0.1 mm cell in PBS at 22° C., between 260–195 nm using a 1 nm bandwidth and a 1 second time constant. The percent helical content was estimated as previously described (Sreerama et al., Anal. Biochem. 209: 32–44 (1993)). Results are shown in Table 2.

TABLE 2

Physical Characteristics of Flt3-L Mutants: Purified Protein

| Mutant | Stokes Radius (x10$^3$) | Percent Helix |
|---|---|---|
| WT | 40.8 | 50 |
| H8R | 40.2 | 50 |
| H8Y | 40.8 | 51 |

TABLE 2-continued

Physical Characteristics of Flt3-L Mutants: Purified Protein

| Mutant | Stokes Radius (x10³) | Percent Helix |
|---|---|---|
| I11Y | 41.1 | 50 |
| L27P | 38.1 | 50 |
| F81S | 41.1 | 50 |
| K84E | 43.5 | 49 |
| K84T | ND | 53 |
| K116E | 45.6 | 49 |
| W118R | 39.4 | 43 |
| Q122R | 38.5 | 51 |

Stokes radius was determined by size exclusion chromatography monitored at an absorbance wavelength of 280 nm, with a 45 µg loading at a concentration of 0.1 mg/ml. The value presented represents at least two measurements and the standard deviation was less than 5% of the reported value. ND stands for "not determined." Percent helix was determined by circular dichroism measurements as described in the text.

With the exception of W118R, none of the mutants analyzed showed gross structural perturbations. Therefore, most of mutations identified are likely in positions of flt3-L that are directly involved in the energetics of receptor binding.

Monomeric unglycosylated flt3-L has a molecular weight of 17,686 daltons. When analyzed by SDS gel electrophoresis, yeast-produced flt3-L migrates at a mass of approximately 21,000 daltons, due to the presence of core glycosylation at a single N-linked site. Stokes radius measurements, as determined by size exclusion chromatography (Mr=40,000), indicate that both the wild type and mutant proteins are dimeric. In addition, the helical content of the wild type and mutant proteins, as determined by their circular dichroism spectra, are similar.

The purified mutants were also subjected to native gel electrophoresis. In all cases, the mobility of the mutant proteins relative to the mobility of wild type protein corresponded to the charge differences associated with the particular amino acid substitution in the mutant protein, confirming that the assessment of substitutions in these mutants is correct.

The helical content of the flt3L mutant polypeptide containing the W118R substitution is 7% less than that of wild type protein. A hydrophobic residue occupies the equivalent site of position 118 of the mature flt3-L polypeptides in murine and human SCF (phenylalanine), and in murine and human M-CSF (leucine), as determined by amino acid sequence alignment. Hannum et al., *Nature* 368:643–648 (1994). In W118R, this hydrophobic residue has been replaced with arginine, a basic residue. Substitution with this basic residue results in a mutant with increased flt3-L biological activity, despite the fact that this mutation disrupts the helical content of flt3-L.

Example 5

Construction and Analysis of Flt3-L Multiple Mutant Polypeptides

Several mutant flt3-L polypeptides containing more than one substitution conferring a flt3-L++ phenotype were constructed. Characteristics of two of these multiple mutant flt3-L polypeptides are shown in Table 3. A mutant containing both the K84E and Q122R substitutions, constructed by subcloning gene fragments, was expressed at near wild type levels. WWF7 cell proliferation assays of supernatants from yeast expressing the K84E/Q122R mutant polypeptide indicated that the total biological activity was equal to the sum of the activities of the K84E and Q122R mutants.

A quadruply substituted flt3-L mutant, L-3H/H8Y/K84E/Q122R, containing the L-3H, H8Y, K84E, and Q122R substitutions, was constructed by PCR mutagenesis, expressed and purified. The 5' oligo JM116.46 (5'-TG-GATAAAAGAcacAGTGGGACCCAGGACTGCTCCTT-CCAATAcag-3') (SEQ ID NO: 6), encoding the L-3H and H8Y substitutions (substituted codons are in lower case), and a 3' vector primer were used to amplify the double mutant K84E/Q122R. A second PCR reaction was used to extend the 5' end using the oligo JM117.42 (5'-TG-GATAAAAGACACAGTGGGACCCAGGACTGCTCC-TTCCAATACAG-3') (SEQ ID NO: 7) and 3' vector primer. The PCR product was introduced into the PIXY456 expression vector by recombination as described above. All constructs were confirmed by DNA sequence analysis. As shown in Table 3, receptor affinity for the purified L-3H/H8Y/K84E/Q122R mutant is over eight times greater than wild type protein, and cell proliferation activity is three times greater.

TABLE 3

Binding and Biological Characteristics of Flt3-L++ Multiple Mutants

| Mutant | Sp.Ac. MUT / Sp.Ac. Wt[a] | $K_{ai}$ MUT / $K_{ai}$ Wt[b] |
|---|---|---|
| WT | 1.0 | 1.0 |
| H8Y | 2.1 ± 0.1 | 2.8 ± 0.1 |
| K84E/Q122R | 2.9 ± 0.7 | 3.4 ± 1.6 |
| L-3H/H8Y/K84E/Q122R | 3.0 ± 1.1 | 8.6 ± 0.8 |

[a]The specific activity of purified mutant or wild type protein was determined by taking the ratio of proliferation activity in BAF/hflt3 cells (units/ml) to concentration of flt3-L protein as determined by amino acid composition (ng/ml). The ratio of specific activity of mutant to wild type flt3-L is averaged over three independent assays, and the standard error of the mean (SEM) is reported.
[b]The $K_{ai}$ for wild type protein is 61 ± 19 pM (n = 2). The ratio of $K_{ai}$ of mutant to wild type flt3-L is averaged over two independent assays and the standard deviation is reported.

Example 6

Modeling of Flt3-L

A model of the quaternary flt3-L structure was generated using FOLDER, a distance geometry-based method for homology modeling. Srinivasun et al., *Protein Sci.* 2:277–289 (1993). FOLDER uses a sequence alignment between a template and model protein to identify residues in topologically equivalent positions. For topologically non-equivalent atoms, such as variable loops and some side chains, chemical constraints, standard geometrical parameters, and chemical information like disulfide cross-links are used to compute a set of distances between these atoms, which is appended to the set of distances for topologically equivalent atoms. The x-ray crystallographic coordinates for M-CSF (Pandit et al., *Science* 258:1358–1362 (1992)) served as the structural template for modelling flt3-L, because M-CSF is the most closely related protein to flt3-L for which a crystal structure has been solved. Flt3-L was modeled with the assumption that the dimer interface would be the same in M-CSF and flt3-L. The computer graphics program Insight was used to generate the images shown in FIG. 4.

Figure 4A:
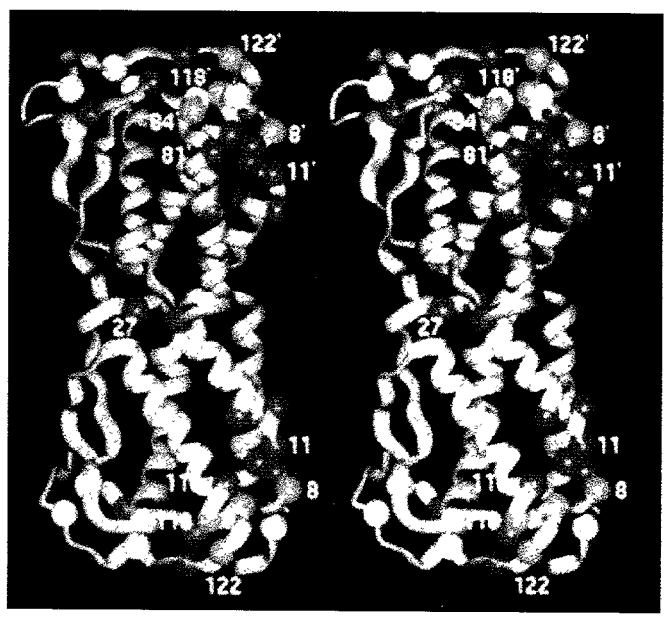
FIGS. 4A and 4B are three dimensional representations of the flt3-L polypeptide.
Figure 4B:
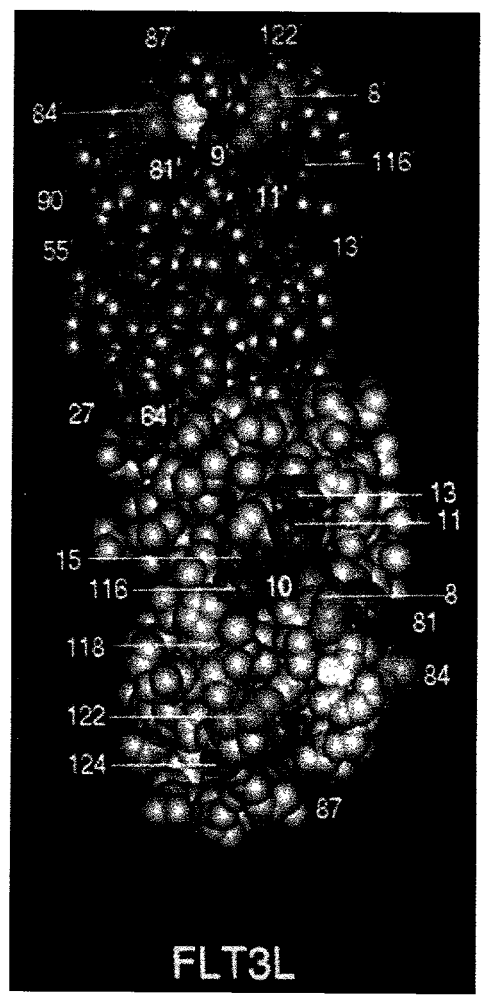

FIG. 4 is a stereo diagram of an α-carbon ribbon trace of flt3-L gold. One subunit is represented in gray, and the other subunit is shown in brown. The axis of dyad symmetry runs approximately horizontal in the plane of the page. The helices of the lower subunit are color coded; the two front helices, A and D are yellow, and the two back helices, B and C, are gold. The α-carbon of specific residues are represented as balls and are color coded; cysteine residues are light yellow, flt3-L- residues are red, and flt3-L$^{++}$ residues are blue. Position 8 is colored blue, although a flt3-L$^-$ mutation also occurs at this site. Flt3-L mutations listed in Table 1 whose activity is greater than wild type or reduced more than 75% of wild type are represented, except the cysteine substitutions R20C and R55C. Position labels represent those proteins that were purified. FIG. 4B is a space-filling model of flt3-L. Orientation, coloration (except helices, which are uniform gold), representation, and numbering are as in FIG. 4A. Flt3L mutations listed in Table 1 whose activity is greater than wild type or reduced more than 75% of wild type are represented and labeled.

As shown in the model, the L27P mutation (SEQ ID NO:13) maps to the predicted dimerization interface of flt3-L. Mutations at the dimerization interface may destabilize flt3-L dimers, resulting in a monomeric flt3-L. Analysis of L27P by size exclusion chromatography indicated that it is dimeric at 0.1 mg/ml (Table 2). To test whether monomeric flt3-L species would be observed at lower concentrations, L27P and wild type flt3-L were diluted and analyzed by size exclusion chromatography. See FIG. 5A (wild type flt3-L) and 5B (L27P). The concentration of flt3-L proteins was 0.28 mg/ml (solid line) or 0.017 mg/ml (dashed line). The detection wavelength was set at 220 nm. A 50-μl injection volume was used, and the low protein concentration peak profile was scaled to allow comparison of elution times from different protein concentrations.

Figure 5A:
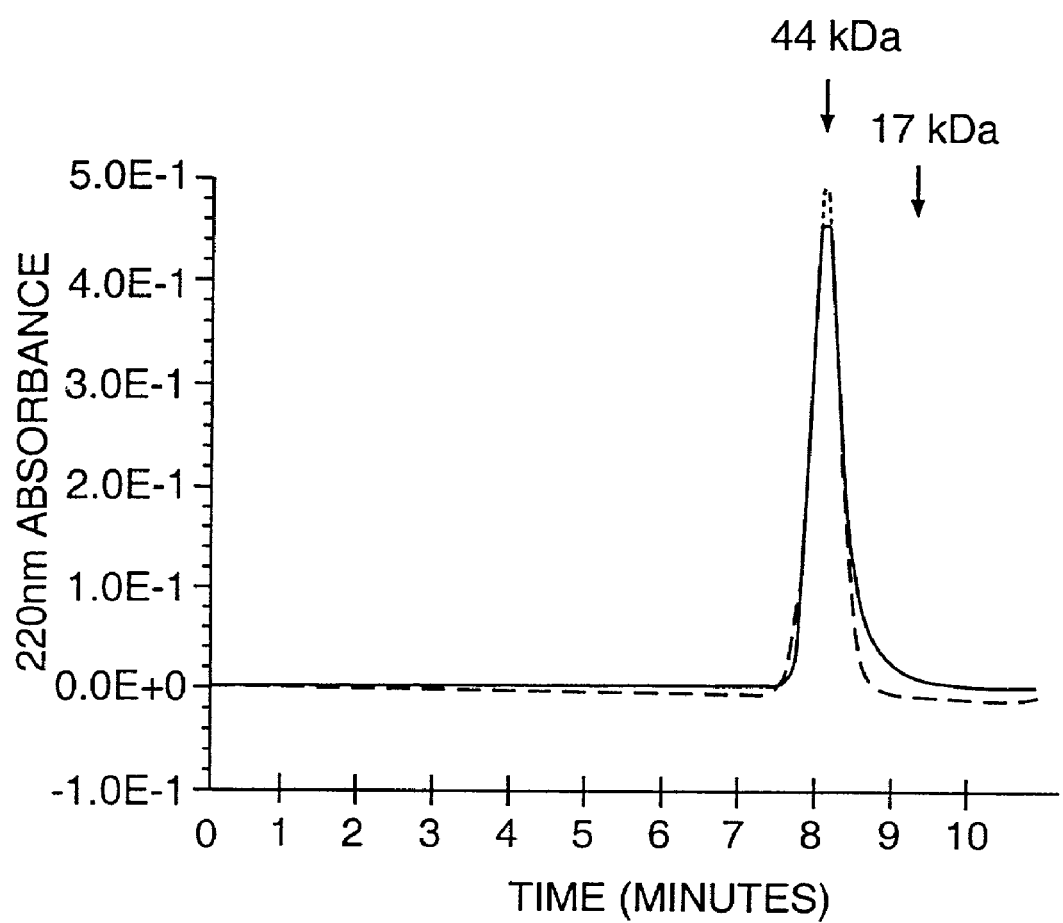
FIGS. 5A and 5B are size exclusion chromatographs of wild type (A) and mutant (B) flt3-L proteins at different concentrations.
Figure 5B:
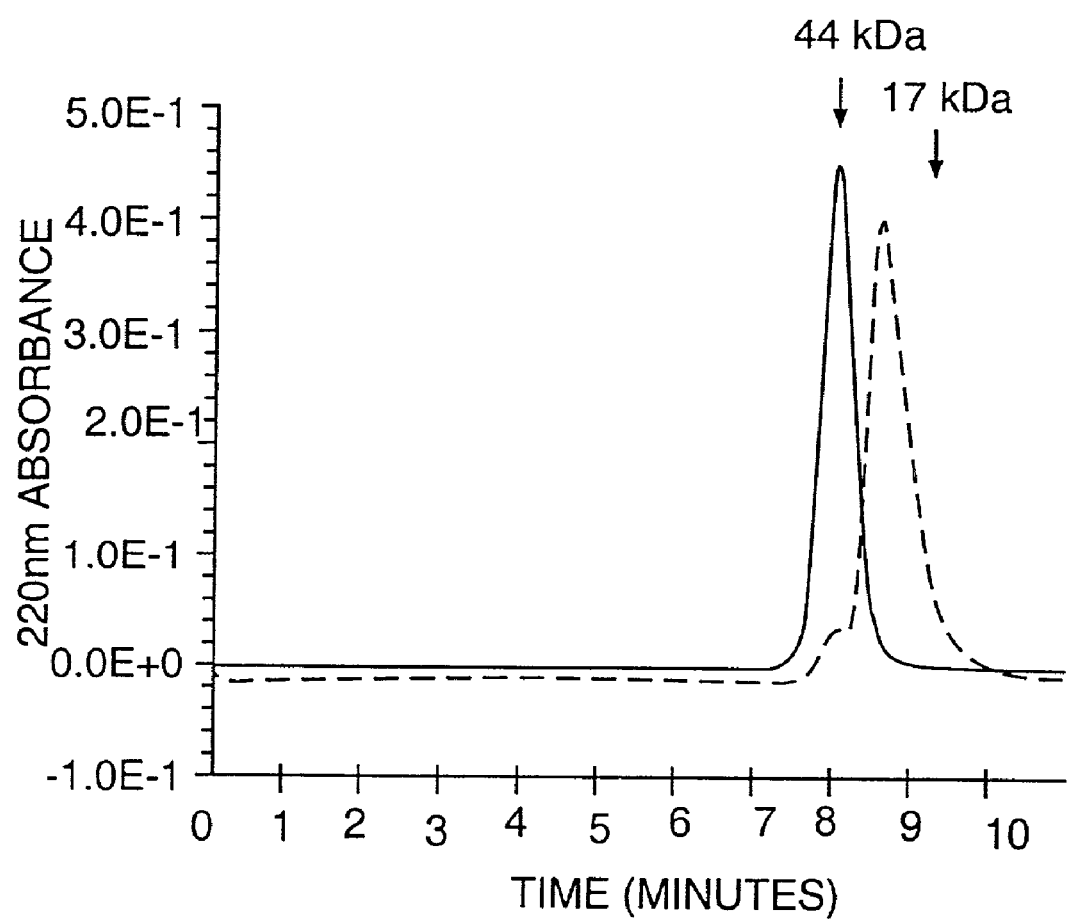

As shown in FIG. 5A, wild type flt3-L eluted at 8.1 min at both concentrations, i.e., at 0.28 or 0.017 mg/ml. At 0.28 mg/ml, the elution time of the L27P protein was nearly identical to the wild type dimeric flt3-L. However, as the concentration of the L27P protein was reduced to 0.017 mg/ml, the peak at 8.1 min was reduced in size, and a second peak was observed at 8.6 min. (FIG. 5B). The change in the elution time of the L27P protein when diluted from 0.28 mg/ml to 0.017 mg/ml corresponds to a shift in the observed molecular weight from 44,000 daltons to 28,000 daltons. In contrast, the wild type flt3-L protein remains at 44,000 daltons for both concentrations. These data indicate that the L27P mutation, which produces a mutant protein that is expressed at high levels, alters the flt3-L dimerization interface, resulting in monomeric flt3-L species at reduced protein concentrations. The fact that the L27P mutation maps to the predicted dimerization interface and alters monomer-dimer equilibrium of the native flt3-L polypeptide validates the M-CSF polypeptide structure as a template for modeling flt3-L structure.

The mutagenesis data and the three-dimensional model of flt3-L corroborate each other. The three hot spot regions (positions 8–15, 81–87, and 116–124 of the mature flt3-L polypeptide, SEQ ID NO:18), widely separated in the primary structure, cluster together in a small surface patch of the tertiary structure. The clustering of mutations in a small surface patch is consistent with a single receptor binding site per monomer as suggested by studies of similar receptor-ligand systems. The model also indicates that some mutations that result in decreased flt3-L biological activity map to the proposed dimer interface. In addition to L27P, the mutations L26F and A64T, which also map to the dimer interface were identified. Alteration of the dimerization interface and reduction in biological activity may be a general phenomenon among four helix bundle cytokines. In the protein sequence alignment proposed by Hannum et al., Nature 368:643–648 (1994), the alanine at position 64 of flt3-L correlates with the Phe at position 64 in SCF. A mutation at Phe$^{67}$ in SCF alters monomer-dimer equilibrium toward monomer and reduces the biological activity of SCF. Hsu etj al., J. Biol. Chem. 272: 6406–6415 (1997).

As noted above, mutations that map to three hot spots scattered throughout the primary sequence cluster together in a patch on the flt3-L three-dimensional model (FIG. 4). The histidine at position 8 of the mature wild type flt3-L polypeptide maps to the center of this patch. Two substitutions for histidine at position 8 were isolated, H8R, which is flt3L$^-$, and H8Y, which is flt3L$^{++}$. This histidine is conserved in murine flt3-L and M-CSF (see FIG. 1). The activity of M-CSF is reduced when the equivalent histidine, at position 9 in the M-CSF polypeptide, is substituted by alanine. High resolution three-dimensional analysis of M-CSF mutant H9A/H15A shows no significant structural perturbations. These data suggest that His$^9$ of M-CSF and His$^8$ of flt3-L are directly involved in the binding energetics with their respective receptors.

The positively charged lysine at position 84 of the mature wild type flt3-L polypeptide is the penultimate residue of the C terminus of helix C. In mutants K84E and K84T, the substitution of this lysine with nonbasic residues results in a flt3-L$^{++}$ phenotype. The threonine substitution of K84T is conservative with the serines found in the equivalent site in M-CSF and murine flt3-L, indicating that Lys$^{84}$ acts to diminish activity in native flt3-L by destabilizing the interaction with flt3.

Inspection of FIG. 5B reveals that K84E, Q122R, and H8Y form a triangle of residues that enhance binding of flt3-L to its receptor. Residues that map within this triangle include Asp$^3$, Cys$^4$, Ser$^5$, and Gln$^7$. Other residues that map within the triangle include Ser$^5$ and Gln$^7$, which are Tyr$^5$ and Ser$^7$ in murine flt3-L, respectively (FIG. 1). Since murine flt3-L stimulates human flt3, these residues are not critical for receptor binding. These data indicate that residues that can be changed to increase receptor affinity also include residues that are not part of a continuous patch, i.e., they are not directly involved in receptor binding. Consistent with this interpretation is the observation that W118R and L-3H increase binding affinity for the flt3 receptor and introduce an extra positive charge to the molecule. The W118R mutation disrupts some of the helical content of the molecule (Table 2), and Leu$^{-3}$ is a residue that is not normally found in the mammalian expressed molecule, so it is unlikely that either residue is part of the flt3 binding site. Thus, the introduction of additional basic residues into the wild type flt3-L polypeptide, or replacement of residues in flt3-L with basic residues, can be used to generate flt3-L mutant polypeptides with increased biological activity.

Example 7

Use of Flt3-L Mutants in Peripheral Stem Cell Transplantation

The flt3-L mutant polypeptides described herein have altered flt3-L biological activity. Some flt3-L mutant polypeptides have greater flt3-L biological activity than wild type flt3-L, as measured by inducement of cellular proliferation. These mutants would therefore be useful in methods of cell expansion and transplantation. In particular, flt3-L mutants exhibiting increased biological activity can be used to expand cells for autologous peripheral stem cell (PSC) or peripheral blood progenitor cell (PBPC) transplantation. Methods for performing these procedures are described in detail in U.S. Pat. No. 5,554,512, hereby incorporated by reference.

PBPC or PSC may be mobilized or increased prior to collection of cells from a patient. This mobilization or increase can be effected by the intravenous administration of a pharmaceutical preparation of flt3-L mutant protein prior to cell collection. Other growth factors such as M-CSF, GM-CSF, SCF, G-CSF, EPO, TPO, IL-1, IL-2, IL-3, IL-4, IL-5, IL-6, IL-7, IL-8, IL-9, IL-10, IL-11, IL-12, IL-13, IL-14, IL-15, GM-CSF/IL-3 fusion proteins, LIF, FGF and combinations thereof, can be administered sequentially or concurrently with the flt3-L mutant polypeptide.

Mobilized or non-mobilized PBPC and PSC are collected using known apheresis procedures. See, e.g., Bishop et al., *Blood*, vol. 83, No. 2, pp. 610–616 (1994). Briefly, PBPC and PSC are collected using conventional devices, such as a Haemonetics Model V50 apheresis device (Haemonetics, Braintree, Mass.). Four-hour collections are performed typically no more than five times weekly until approximately $6.5 \times 10^8$ mononuclear cells (MNC)/kg patient are collected. Aliquots of collected PBPC and PSC are assayed for granulocyte-macrophage colony-forming unit (CFU-GM) content by diluting the cells approximately 1:6 with Hank's balanced salt solution without calcium or magnesium (HBSS) and layering over lymphocyte separation medium (Organon Teknika, Durham, N.C.). Following centrifugation, MNC at the interface are collected, washed and resuspended in HBSS. One milliliter aliquots containing approximately 300,000 MNC, modified McCoy's 5A medium, 0.3% agar, 200 U/mL recombinant human GM-CSF, 200 u/mL recombinant human IL-3, and 200 u/mL recombinant human G-CSF are cultured at 37° C. in 5% $CO_2$ in fully humidified air for 14 days. Optionally, a flt3-L mutant polypeptide or GM-CSF/IL-3 fusion molecules (PIXY 321) may be added to the cultures. These cultures are stained with Wright's stain, and CFU-GM colonies are scored using a dissecting microscope (Ward et al., *Exp. Hematot.*, 16:358 (1988)). Alternatively, CFU-GM colonies can be assayed using the CD34/CD33 flow cytometry method of Siena et al., *Blood*, Vol. 77, No. 2, pp 400–409 (1991), or any other method known in the art.

CFU-GM containing cultures can be frozen in a controlled rate freezer (e.g., Cryo-Med, Mt. Clemens, Mich.), then stored in the vapor phase of liquid nitrogen. Ten percent dimethylsulfoxide can be used as a cryoprotectant. After all collections from the patient have been made, CFU-GM-containing cultures are thawed and pooled. The pooled cells may be then be expanded ex vivo, prior to intravenous infusion into a patient. Ex vivo expansion of pooled cells can be performed using a mutant flt3-L polypeptide as a growth factor either alone, sequentially or in concurrent combination with other cytokines listed above, using methods that are well known in the art. To facilitate engraftment of the transplanted cells, a mutant flt3-L polypeptide may be administered simultaneously with, or subsequent to, the infusion, either alone, sequentially or in concurrent combination with other cytokines selected from the list above.

Example 8

Generation of Dendritic Cells in vitro

Stem cells, e.g., cells having the $CD34^+$ phenotype, are isolated as described above, for example, first by generating a buffy coat of cells. Cells from the buffy coat are then incubated with a CD34 specific monoclonal antibody. The selected $CD34^+$ cells are then cultured in McCoy's enhanced media with 20 ng/ml each of GM-CSF, IL4, TNF-α, or 100 ng/ml flt3-L or c-kit ligand. The culture is continued for approximately two weeks at 37° C. in 10% $CO_2$ in humid air. Cells then are sorted by flow cytometry for $CD1\ a^+$ and $HLA-DR^+$ expression.

Example 9

Use of Flt3-L Mutant Polypeptides to Promote Dendritic Cell Expansion

This Example describes a method for using flt3-L mutant polypeptides for dendritic cell expansion. Prior to cell collection, it may be desirable to mobilize or increase the numbers of circulating PBPC and PBSC. Mobilization can improve PBPC and PBSC collection, and is achievable through the intravenous administration of flt3-ligand or sargramostim (Leukine®, Immunex Corporation, Seattle, Wash.) to a patient prior to collection of such cells. Other growth factors such as M-CSF, GM-CSF, SCF, G-CSF, EPO, TPO, IL-1, IL-2, IL-3, IL-4, IL-5, IL-6, IL-7, IL-8, IL-9, IL-10, IL-11, IL-12, IL-13, IL-14, IL-15, GM-CSF/IL-3 fusion proteins, LIF, FGF and combinations thereof, can be likewise administered in sequence, or in concurrent combination with flt3-L. Mobilized or non-mobilized PBPC and PBSC are collected using apheresis procedures known in the art. See, for example, Bishop et al., *Blood*, vol. 83, No. 2, pp. 610–616 (1994). Briefly, PBPC and PBSC are collected using conventional devices, for example, a Haemonetics Model V50 apheresis device (Haemonetics, Braintree, Mass.). Four-hour collections are performed typically no more than five times weekly until approximately $6.5 \times 10^8$ mononuclear cells (MNC)/kg patient are collected. Aliquots of collected PBPC and PBSC are assayed for granulocyte-macrophage colony-forming unit (CFU-GM) content by diluting approximately 1:6 with Hank's balanced salt solution without calcium or magnesium (HBSS) and layering over lymphocyte separation medium (Organon Teknika, Durham, N.C.) Following centrifugation, MNC at the interface are collected, washed and resuspended in HBSS. One milliliter aliquots containing approximately 300,000 MNC, modified McCoy's 5A medium, 0.3% agar, 200 U/mL recombinant human GM-CSF, 200 u/mL recombinant human IL-3, and 200 u/mL recombinant human G-CSF or GM-CSF/IL-3 fusion molecules (PIXY 321) may be added to the cultures. These cultures are stained with Wright's stain, and CFU-GM colonies are scored using a dissecting microscope (Ward et al., *Exp. Hematol.*, 16:358 (1988)). Alternatively, CFU-GM colonies can be assayed using the CD34/CD33 flow cytometry method of Siena et al., *Blood*, Vol. 77, No. 2, pp. 400–409 (1991), or any other method know in the art.

CFU-GM containing cultures are frozen in a controlled rate freezer (e.g., Cryo-Med, Mt. Clemens, Mich.), then stored in the vapor phase of liquid nitrogen. Ten percent dimethylsulfoxide can be used as a cryoprotectant. After all collections from the patient have been made, CFU-GM containing cultures are thawed and pooled. The thawed cell collection is contacted with a flt3-L mutant polypeptide, either alone, sequentially or in concurrent combination with other cytokines listed above. Such exposure to flt3-L mutant polypeptides will drive the CFU-GM to differentiate into dendritic cells. The expanded dendritic cell population is then administered to the patient, e.g., intravenously.

What is claimed is:

1. A method of inducing cellular expansion, comprising the steps of:
   isolating a population of cells to be expanded; and
   exposing said cells to a soluble mutant flt3-L polypeptide to produce an expanded cell population, wherein said polypeptide comprises a substitution at one or more residues corresponding to amino acid position 24 of the full length human wild type flt3-L polypeptide (SEQ ID NO:1) or amino acid positions 8–15, 81–87 or 116–124 of the mature human wild type flt3-L polypeptide (SEQ ID NO:18), wherein the mutant flt3-L polypeptide exhibits increased biological activity relative to full length wild type (SEQ ID NO:1) or mature human wild type (SEQ ID NO:18) flt3-L polypeptide.

2. The method of claim 1, wherein the expanded cell population is introduced into a patient.

3. The method of claim 1, wherein the population of cells to be expanded comprises hematopoietic cells.

4. The method of claim 1, wherein the population of cells is also exposed to a growth factor in addition to said flt3-L mutant polypeptide.

5. The method of claim 1, wherein said growth factor is selected from the group consisting of interleukins, colony stimulating factors, and protein kinases.

6. The method according to claim 1, wherein a basic amino acid within amino acid positions 8–15 or 81–87 of the mature human wild type flt3-L polypeptide (SEQ ID NO:18) has been replaced with a non-basic amino acid or wherein an amino acid within amino acid positions 116–124 of the mature human wild type flt3-L polypeptide (SEQ ID NO:18) has been replaced with a basic amino acid.

7. The method according to claim 6, wherein the basic amino acid replaced within amino acid positions 8–15 or 81–87 is the His at position 8 or the Lys at position 84 of the mature human wild type flt3-L (SEQ ID NO:18).

8. The method according to claim 6, wherein the amino acid replaced within amino acid positions 116–124 is the Trp at position 118 or the Gln at position 122 of the mature human wild type flt3-L (SEQ ID NO:18).

9. The method according to claim 1, wherein a second polypeptide is fused to the soluble mutant flt3-L polypeptide, wherein said second polypeptide is erythropoietin (EPO), thrombopoietin (TPO), granulocyte-macrophage Colony Stimulating Factor (GM-CSF), granulocyte Colony Stimulating Factor (G-CSF), an interleukin, an immunoglobulin, or fragments thereof, wherein the fragments retain the biological activity of the second polypeptide.

10. The method according to claim 1, wherein said substitution at one or more residues corresponds to amino acid positions 8, 84, 118 or 122 of the mature human wild type flt3-L polypeptide (SEQ ID NO:18).

11. The method according to claim 1, wherein said soluble mutant flt3-L polypeptide comprises one or more substitutions corresponding to L1H (SEQ ID NO:10), H8Y (SEQ ID NO:11), W118R (SEQ ID NO:16), K84E (SEQ ID NO:14), K84T (SEQ ID NO:15) or Q122R (SEQ ID NO:17).

12. The method according to claim 1, wherein said soluble mutant flt3-L polypeptide comprises amino acids 28–160, 28–182 or 28–185 of the full length human wild type flt3-L polypeptide (SEQ ID NO:1).

13. The method according to claim 1, wherein the population of cells to be expanded comprise CD34+ hematopoietic stem cells, hematopoietic progenitor cells, hematopoietic stem and progenitor cells or dendritic cells.

14. The method of claim 13, wherein the expanded cell population is introduced into a patient.

15. A method of expanding a population of cells in vivo, comprising the step of administering to a subject a pharmaceutical composition of a soluble mutant flt3-L polypeptide sufficient to induce the expansion of a target cell population, wherein said polypeptide comprises a substitution at one or more residues corresponding to amino acid position 24 of the full length human wild type flt3-L polypeptide (SEQ ID NO:1) or amino acid positions 8–15, 81–87 or 116–124 of the mature human wild type flt3-L polypeptide (SEQ ID NO:18), wherein the mutant flt3-L polypeptide exhibits increased biological activity relative to full length wild type (SEQ ID NO:1) or mature human wild type (SEQ ID NO:18) flt3-L polypeptide.

16. The method of claim 15, wherein the target cell population comprises hematopoietic cells or dendritic cells.

17. The method according to claim 16, wherein the hematopoietic cells comprise hematopoietic stem cells, hematopoietic progenitor cells, or hematopoietic stem and progenitor cells.

18. The method according to claim 17, wherein the hematopoietic cells are CD34+.

19. The method of claim 15, wherein the pharmaceutical composition further comprises a growth factor in addition to said flt3-L mutant polypeptides.

20. The method of claim 19, wherein said growth factor is selected from the group consisting of interleukins, colony stimulating factors and protein kinases.

21. The method according to claim 15, wherein a basic amino acid within amino acid positions 8–15 or 81–87 of the mature human wild type flt3-L polypeptide (SEQ ID NO:18) has been replaced with a non-basic amino acid or wherein an amino acid within amino acid positions 116–124 of the mature human wild type flt3-L polypeptide (SEQ ID NO:18) has been replaced with a basic amino acid.

22. The method according to claim 21, wherein the basic amino acid replaced within amino acid positions 8–15 or 81–87 is the His at position 8 or the Lys at position 84 of the mature human wild type flt3-L (SEQ ID NO:18).

23. The method according to claim 21, wherein the amino acid replaced within amino acid positions 116–124 is the Trp at position 118 or the Gln at position 122 of the mature human wild type flt3-L (SEQ ID NO:18).

24. The method according to claim 15, wherein a second polypeptide is fused to the soluble mutant flt3-L polypeptide, wherein said second polypeptide is erythropoietin (EPO), thrombopoietin (TPO), granulocyte-macrophage Colony Stimulating Factor (GM-CSF), granulocyte Colony Stimulating Factor (G-CSF), an interleukin, an immunoglobulin, or fragments thereof, wherein the fragments retain the biological activity of the second polypeptide.

25. The method according to claim 15, wherein said substitution at one or more residues corresponds to amino acid positions 8, 84, 118 or 122 of the mature human wild type flt3-L polypeptide (SEQ ID NO:18).

26. The method according to claim 15, wherein said soluble mutant flt3-L polypeptide comprises one or more substitutions corresponding to L1H (SEQ ID NO:10), H8Y (SEQ ID NO:11), W118R (SEQ ID NO:16), K84E (SEQ ID NO:14), K84T (SEQ ID NO:15) or Q122R (SEQ ID NO:17).

27. The method according to claim 15, wherein said soluble mutant flt3-L polypeptide comprises amino acids 28–160, 28–182 or 28–185 of the full length human wild type flt3-L polypeptide (SEQ ID NO:1).

28. A method for transplanting hematopoietic stem cells, progenitor cells or both hematopoietic stem cells and progenitor cells in a patient in need thereof, comprising:
  (a) administering a therapeutically effective amount of a pharmaceutical composition comprising a soluble flt3-L mutant polypeptide to the patient to expand the hematopoietic stem cells, progenitor cells or both in the patient, wherein said polypeptide has a substitution at one or more residues corresponding to amino acid position 24 of the full length human wild type flt3-L polypeptide (SEQ ID NO:1) or amino acid positions 8–15, 81–87 or 116–124 of the mature human wild type flt3-L polypeptide (SEQ ID NO:18) wherein the mutant flt3-L polypeptide exhibits increased biological activity relative to full length wild type (SEQ ID NO:1) or mature human wild type (SEQ ID NO:18) flt3-L polypeptide;
  (b) collecting said expanded hematopoietic stem cells, progenitor cells or both from the patient; and
  (c) transplanting said cells collected in step (b) to the patient.

29. The method according to claim 28, further comprising administering radiation, chemotherapy or both radiation and chemotherapy to the patient, wherein said cells are transplanted concurrent with or following administering radiation, chemotherapy or both.

30. The method according to claim 28, wherein the hematopoietic stem cells or progenitor cells are allogeneic.

31. The method according to claim 28, wherein the hematopoietic stem cells or progenitor cells are autologous.

32. The method according to claim 28, wherein a basic amino acid within amino acid positions 8–15 or 81–87 of the mature human wild type flt3-L polypeptide (SEQ ID NO:18) has been replaced with a non-basic amino acid, or wherein an amino acid within amino acid positions 116–124 of the mature human wild type flt3-L polypeptide (SEQ ID NO:18) has been replaced with a basic amino acid.

33. The method according to claim 32, wherein a basic amino acid replaced within amino acid positions 8–15 or 81–87 is the His at position 8 or the Lys at position 84 of the mature human wild type flt3-L (SEQ ID NO:18).

34. The method according to claim 32, wherein the amino acid replaced within amino acid positions 116–124 is the Trp at position 118 or the Gln at position 122 of the mature human wild type flt3-L (SEQ ID NO:18).

35. The method according to claim 28, wherein a second polypeptide is fused to the soluble mutant flt3-L polypeptide, wherein said second polypeptide is erythropoietin (EPO), thrombopoietin (TPO), granulocyte-macrophage Colony Stimulating Factor (GM-CSF), granulocyte Colony Stimulating Factor (G-CSF), an inteileukin, an immunoglobulin, or fragments thereof, wherein the fragments retain the biological activity of the second polypeptide.

36. The method according to claim 28, wherein said substitution at one or more residues corresponds to amino acid positions 8, 84, 118 or 122 of the mature human wild type flt3-L polypeptide (SEQ ID NO:18).

37. The method according to claim 28, wherein said soluble mutant flt3-L polypeptide has one or more substitutions corresponding to L1H (SEQ ID NO:10), H8Y (SEQ ID NO:11), W118R (SEQ ID NO:16), K84E (SEQ ID NO:14), K84T (SEQ ID NO:15) or Q122R (SEQ ID NO:17).

38. The method according to claim 28, wherein said soluble mutant flt3-L polypeptide comprises amino acids 28–160, 28–182 or 28–185 of the full length human wild type flt3-L polypeptide (SEQ ID NO:1).

39. The method of claim 28, further comprising administering said composition to the patient after transplanting said cells to the patient.

40. A method for transplanting hematopoietic stem cells, progenitor cells or both hematopoietic stem cells and progenitor cells in a patient in need thereof, comprising:
  (a) collecting hematopoietic cells, progenitor cells or both from the patient;
  (b) administering ex vivo an effective amount of a composition comprising a soluble flt3-L mutant polypeptide to said cells collected in step (a) to expand the hematopoietic stem cells, progenitor cells or both, wherein said polypeptide has a substitution at one or more residues corresponding to amino acid position 24 of the full length human wild type flt3-L polypeptide (SEQ ID NO:1) or amino acid positions 8–15, 81–87 or 116–124 of the mature human wild type flt3-L polypeptide (SEQ ID NO:18) wherein the mutant flt3-L polypeptide exhibits increased biological activity relative to full length wild type (SEQ ID NO:1) or mature human wild type (SEQ ID NO:18) flt3-L polypeptide; and (c) transplanting said expanded hematopoietic stem cells, progenitor cells or both to the patient.

41. The method according to claim 40, further comprising administering radiation, chemotherapy or both radiation and chemotherapy to the patient, wherein said cells are transplanted concurrent with or following administering radiation, chemotherapy or both.

42. The method according to claim 40, wherein the hematopoietic stem cells or progenitor cells are allogeneic.

43. The method according to claim 40, wherein the hematopoietic stem cells or progenitor cells are autologous.

44. The method according to claim 40, wherein a basic amino acid within amino acid positions 8–15 or 81–87 of the mature human wild type flt3-L polypeptide (SEQ ID NO:18) has been replaced with a non-basic amino acid, or wherein an amino acid within amino acid positions 116–124 of the mature human wild type flt3-L polypeptide (SEQ ID NO:18) has been replaced with a basic amino acid.

45. The method according to claim 44, wherein the basic amino acid replaced within amino acid positions 8–15 or 81–87 is the His at position 8 or the Lys at position 84 of the mature human wild type flt3-L (SEQ ID NO:18).

46. The method according to claim 44, wherein the amino acid replaced within amino acid positions 116–124 is the Trp at position 118 or the Gln at position 122 of the mature human wild type flt3-L (SEQ ID NO:18).

47. The method according to claim 40, wherein a second polypeptide is fused to the soluble mutant flt3-L polypeptide, wherein said second polypeptide is erythropoietin (EPO), thrombopoietin (TPO), granulocyte-macrophage Colony Stimulating Factor (GM-CSF), granulocyte Colony Stimulating Factor (G-CSF), an interleukin, an immunoglobulin, or fragments thereof, wherein the fragments retain the biological activity of the second polypeptide.

48. The method according to claim 40, wherein said substitution at one or more residues corresponds to amino acid positions 8, 84, 118 or 122 of the mature human wild type flt3-L polypeptide (SEQ ID NO:18).

49. The method according to claim 40, wherein said soluble mutant flt3-L polypeptide has one or more substitutions corresponding to L1H (SEQ ID NO:10), H8Y (SEQ ID NO:11), W118R (SEQ ID NO:16), K84E (SEQ ID NO:14), K84T (SEQ ID NO:15) or Q122R (SEQ ID NO:17).

50. The method according to claim 40, wherein said soluble mutant flt3-L polypeptide comprises amino acids 28–160, 28–182 or 28–185 of the full length human wild type flt3-L polypeptide (SEQ ID NO:1).

51. The method according to claim 40, further comprising administering said composition to the patient prior to collecting the hematopoietic cells from the patient.

52. The method according to claim 40, further comprising administering said composition to the patient after transplanting the hematopoietic stem cells, progenitor cells or both to the patient.

53. The method according to claim 40, wherein the hematopoietic cells are collected from peripheral blood, umbilical cord blood or bone marrow.

54. The method according to claim 40, wherein the hematopoietic stem cells, progenitor cells or both are $CD34^+$.

* * * * *